(12) United States Patent
Devgon et al.

(10) Patent No.: US 10,300,247 B2
(45) Date of Patent: May 28, 2019

(54) DEVICES AND METHODS FOR FLUID TRANSFER THROUGH A PLACED PERIPHERAL INTRAVENOUS CATHETER

(71) Applicant: Velano Vascular, Inc., San Francisco, CA (US)

(72) Inventors: Pitamber Devgon, Philadelphia, PA (US); Kevin J. Ehrenreich, San Francisco, CA (US); Richard Thomas Briganti, Bala Cynwyd, PA (US)

(73) Assignee: VELANO VASCULAR, INC., San Francisco, CA (US)

( * ) Notice: Subject to any disclaimer, the term of this patent is extended or adjusted under 35 U.S.C. 154(b) by 309 days.

(21) Appl. No.: 15/014,834

(22) Filed: Feb. 3, 2016

(65) Prior Publication Data
US 2017/0216564 A1 Aug. 3, 2017

(51) Int. Cl.
*A61B 5/15* (2006.01)
*A61M 25/01* (2006.01)
*A61M 25/06* (2006.01)

(52) U.S. Cl.
CPC ..... *A61M 25/0606* (2013.01); *A61B 5/15003* (2013.01); *A61B 5/150259* (2013.01);
(Continued)

(58) Field of Classification Search
CPC .......... A61B 5/15003; A61B 5/150259; A61B 5/150992; A61M 25/0606; A61M 25/01;
(Continued)

(56) References Cited

U.S. PATENT DOCUMENTS

| 4,192,319 A | 3/1980 | Hargens et al. |
| 4,314,555 A | 2/1982 | Sagae |
(Continued)

FOREIGN PATENT DOCUMENTS

| EP | 2504054 | 9/2013 |
| JP | S55-119739 U | 8/1980 |
(Continued)

OTHER PUBLICATIONS

Office Action for U.S. Appl. No. 13/456,900, dated Sep. 5, 2012, 11 pages.
(Continued)

*Primary Examiner* — Laura A Bouchelle
*Assistant Examiner* — Dung T Ulsh
(74) *Attorney, Agent, or Firm* — Cooley LLP

(57) ABSTRACT

An apparatus includes a catheter, an introducer, and an actuator. A distal end portion of the introducer is configured to be coupled to a peripheral intravenous line. The introducer defines an inner volume having a first portion that defines an axis parallel to and offset from an axis defined by a second portion. A first portion of the actuator is movably disposed in the first portion of the inner volume. A second portion of the actuator is movably disposed in the second portion of the inner volume and coupled to the catheter movably disposed in the second portion of the inner volume. The actuator moves the catheter between a first position, in which the catheter is disposed within the introducer, and a second position, in which at least a portion of the catheter is disposed within the peripheral intravenous line.

37 Claims, 18 Drawing Sheets

(52) U.S. Cl.
CPC ... *A61B 5/150992* (2013.01); *A61M 25/0113* (2013.01); *A61M 25/0111* (2013.01); *A61M 2025/0681* (2013.01)

(58) Field of Classification Search
CPC ...... A61M 25/0102; A61M 2025/0175; A61M 25/0625; A61M 25/09041; A61M 2025/09125; A61M 25/0617; A61M 25/0631
See application file for complete search history.

(56) References Cited

U.S. PATENT DOCUMENTS

| | | | |
|---|---|---|---|
| 4,790,830 A | 12/1988 | Hamacher |
| 4,808,158 A | 2/1989 | Kreuzer et al. |
| 4,808,165 A | 2/1989 | Carr |
| 4,935,010 A | 6/1990 | Cox et al. |
| 5,013,304 A | 5/1991 | Russell et al. |
| 5,100,390 A | 3/1992 | Lubeck et al. |
| 5,135,502 A | 8/1992 | Koenig, Jr. et al. |
| 5,147,334 A | 9/1992 | Moss |
| 5,201,722 A | 4/1993 | Moorehead et al. |
| 5,203,771 A | 4/1993 | Melker et al. |
| 5,270,003 A | 12/1993 | Bernes et al. |
| 5,360,407 A | 11/1994 | Leonard |
| 5,368,029 A | 11/1994 | Holcombe et al. |
| 5,552,118 A | 9/1996 | Mayer |
| 5,553,625 A | 9/1996 | Rao |
| 5,562,631 A | 10/1996 | Bogert |
| 5,611,782 A | 3/1997 | Haedt |
| 5,658,263 A | 8/1997 | Dang |
| D384,741 S | 10/1997 | Musgrave et al. |
| 5,713,876 A | 2/1998 | Bogert et al. |
| 5,749,857 A | 5/1998 | Cuppy |
| 5,755,709 A | 5/1998 | Cuppy |
| 5,827,229 A | 10/1998 | Auth et al. |
| 5,848,996 A | 12/1998 | Eldor |
| 5,853,393 A | 12/1998 | Bogert |
| 5,897,537 A | 4/1999 | Berg et al. |
| 5,911,715 A | 6/1999 | Berg et al. |
| 5,944,690 A | 8/1999 | Falwell et al. |
| 5,944,695 A | 8/1999 | Johnson et al. |
| 6,036,677 A | 3/2000 | Javier et al. |
| 6,059,759 A | 5/2000 | Mottola et al. |
| 6,080,138 A | 6/2000 | Lemke et al. |
| 6,093,177 A | 7/2000 | Javier et al. |
| 6,126,618 A | 10/2000 | Bischof |
| 6,197,001 B1 | 3/2001 | Wilson et al. |
| 6,508,790 B1 | 1/2003 | Lawrence |
| 6,585,703 B1 | 7/2003 | Kassel et al. |
| 6,648,835 B1 | 11/2003 | Shemesh |
| 6,652,507 B2 | 11/2003 | Pepin |
| 6,685,664 B2 | 2/2004 | Levin et al. |
| 6,692,473 B2 | 2/2004 | St Cyr et al. |
| 6,712,790 B1 | 3/2004 | Prestidge et al. |
| 6,719,726 B2 | 4/2004 | Meng et al. |
| 6,719,781 B1 | 4/2004 | Kim |
| 6,722,370 B1 | 4/2004 | Mann |
| 6,755,812 B2 | 6/2004 | Peterson et al. |
| 6,858,024 B1 | 2/2005 | Berg et al. |
| 6,908,459 B2 | 6/2005 | Harding et al. |
| 7,135,008 B2 | 11/2006 | O'Mahony et al. |
| 7,252,654 B2 | 8/2007 | VanTassel et al. |
| 7,311,689 B2 | 12/2007 | Levin et al. |
| 7,316,678 B2 | 1/2008 | Nash et al. |
| 7,462,161 B2 | 12/2008 | O'Mahony et al. |
| 7,615,033 B2 | 11/2009 | Leong |
| 7,625,367 B2 | 12/2009 | Adams et al. |
| 7,662,110 B2 | 2/2010 | Flaherty |
| 7,670,320 B2 | 3/2010 | Iwase et al. |
| 7,685,367 B2 | 3/2010 | Ruia et al. |
| 7,691,088 B2 | 4/2010 | Howell |
| 7,713,250 B2 | 5/2010 | Harding et al. |
| 7,717,882 B2 | 5/2010 | Harding |
| 7,717,899 B2 | 5/2010 | Bowe et al. |
| 7,762,977 B2 | 7/2010 | Porter et al. |
| 7,766,961 B2 | 8/2010 | Patel et al. |
| 7,771,394 B2 | 8/2010 | Shue et al. |
| 7,892,208 B2 | 2/2011 | Schnell et al. |
| 7,972,294 B2 | 7/2011 | Nash et al. |
| 8,062,226 B2 | 11/2011 | Moore |
| 8,092,374 B2 | 1/2012 | Smith et al. |
| 8,104,475 B2 | 1/2012 | Cheung |
| 8,114,057 B2 | 2/2012 | Gerdts et al. |
| 8,251,978 B2 | 8/2012 | Nash et al. |
| 8,267,911 B2 | 9/2012 | Gallogly et al. |
| 8,361,013 B2 | 1/2013 | Wood |
| 8,361,014 B2 | 1/2013 | Wood |
| 8,366,685 B2 | 2/2013 | Devgon |
| 8,372,032 B2 | 2/2013 | Wood |
| 8,425,532 B2 | 4/2013 | Flom et al. |
| 8,444,605 B2 | 5/2013 | Kuracina et al. |
| 8,491,568 B2 | 7/2013 | Schertiger et al. |
| 8,523,801 B2 | 9/2013 | Nash et al. |
| 8,690,833 B2 | 4/2014 | Belson |
| 8,696,639 B2 | 4/2014 | Smith et al. |
| 8,702,658 B2 | 4/2014 | Spearman |
| 8,721,546 B2 | 5/2014 | Belson |
| 8,728,035 B2 | 5/2014 | Warring et al. |
| 8,728,038 B2 | 5/2014 | Spearman |
| 8,728,058 B2 | 5/2014 | Schertiger |
| 8,753,312 B2 | 6/2014 | Bowe et al. |
| 8,808,246 B2 | 8/2014 | Cabot |
| 8,876,773 B2 | 11/2014 | Ishida |
| 9,186,100 B2 | 11/2015 | Devgon |
| 9,352,128 B2 | 5/2016 | Ishida |
| 9,415,185 B2 | 8/2016 | Notter |
| 9,744,344 B1 | 8/2017 | Devgon et al. |
| 9,750,446 B2 | 9/2017 | Devgon |
| 2002/0120215 A1 | 8/2002 | Crawford et al. |
| 2003/0083620 A1 | 5/2003 | Luther et al. |
| 2004/0092879 A1 | 5/2004 | Kraus et al. |
| 2004/0138622 A1 | 7/2004 | Palasis |
| 2004/0181192 A1 | 9/2004 | Cuppy |
| 2005/0015048 A1 | 1/2005 | Chiu et al. |
| 2005/0090801 A1* | 4/2005 | Racz ............... A61M 25/0097 604/500 |
| 2005/0119597 A1 | 6/2005 | O'Mahony et al. |
| 2005/0165355 A1 | 7/2005 | Fitzgerald |
| 2005/0192558 A1 | 9/2005 | Bernard et al. |
| 2006/0015068 A1 | 1/2006 | Amisar et al. |
| 2006/0142694 A1 | 6/2006 | Bednarek et al. |
| 2007/0088279 A1 | 4/2007 | Shue et al. |
| 2007/0219460 A1 | 9/2007 | Goldenberg |
| 2007/0282280 A1 | 12/2007 | Tennican |
| 2008/0033396 A1 | 2/2008 | Danek et al. |
| 2008/0045862 A1 | 2/2008 | Dalebout et al. |
| 2008/0287918 A1 | 11/2008 | Rosenman et al. |
| 2008/0300574 A1* | 12/2008 | Belson ............. A61M 25/0606 604/510 |
| 2008/0319387 A1 | 12/2008 | Amisar et al. |
| 2009/0156963 A1 | 6/2009 | Noble et al. |
| 2010/0210934 A1 | 8/2010 | Belson |
| 2010/0286657 A1 | 11/2010 | Heck |
| 2010/0305519 A1 | 12/2010 | McKinnon et al. |
| 2011/0015577 A1 | 1/2011 | Baney et al. |
| 2012/0041392 A1 | 2/2012 | Donawick |
| 2012/0046648 A1 | 2/2012 | Scheckel |
| 2012/0053523 A1 | 3/2012 | Harding |
| 2012/0109079 A1 | 5/2012 | Asleson et al. |
| 2012/0191010 A1 | 7/2012 | Cabot |
| 2013/0102888 A1 | 4/2013 | Slim |
| 2013/0131597 A1* | 5/2013 | Blaivas ............ A61M 25/0097 604/173 |
| 2013/0281925 A1 | 10/2013 | Benscoter et al. |
| 2014/0012085 A1 | 1/2014 | Smith et al. |
| 2014/0046214 A1 | 2/2014 | Devgon |
| 2014/0100529 A1* | 4/2014 | Ito ..................... A61M 5/158 604/164.08 |
| 2014/0107427 A1 | 4/2014 | Chow et al. |
| 2014/0107800 A1 | 4/2014 | Flom et al. |
| 2014/0128774 A1 | 5/2014 | Andreae et al. |
| 2014/0128775 A1 | 5/2014 | Andreae et al. |
| 2014/0171803 A1 | 6/2014 | Van Hoven et al. |

(56) References Cited

U.S. PATENT DOCUMENTS

| | | | |
|---|---|---|---|
| 2014/0180127 A1 | 6/2014 | Meyer et al. | |
| 2014/0188002 A1 | 7/2014 | Close et al. | |
| 2014/0188003 A1 | 7/2014 | Belson | |
| 2014/0194833 A1* | 7/2014 | Andrus | A61B 17/0218 |
| | | | 604/288.02 |
| 2014/0296745 A1 | 10/2014 | Cash | |
| 2014/0343456 A1 | 11/2014 | Cabot | |
| 2014/0358120 A1 | 12/2014 | Haarala et al. | |
| 2014/0364766 A1* | 12/2014 | Devgon | A61B 5/15003 |
| | | | 600/581 |
| 2014/0378867 A1 | 12/2014 | Belson | |
| 2015/0005669 A1 | 1/2015 | Burkholz | |
| 2015/0038909 A1 | 2/2015 | Christensen et al. | |
| 2015/0065952 A1 | 3/2015 | Pacheco et al. | |
| 2015/0119859 A1* | 4/2015 | Cajamarca | A61M 25/0012 |
| | | | 604/526 |
| 2015/0148747 A1 | 5/2015 | Whitley | |
| 2015/0313526 A1 | 11/2015 | Van Wieren | |
| 2015/0360005 A1 | 12/2015 | Arellano Cabrera et al. | |
| 2016/0015945 A1 | 1/2016 | Warring et al. | |
| 2016/0022963 A1 | 1/2016 | Belson | |
| 2016/0073937 A1 | 3/2016 | Burkholz et al. | |
| 2016/0166772 A1* | 6/2016 | Mirzazadeh | A61M 5/31526 |
| | | | 604/222 |
| 2016/0206858 A1 | 7/2016 | Ishida | |
| 2016/0220786 A1 | 8/2016 | Mitchell et al. | |
| 2016/0220790 A1 | 8/2016 | Borowicz | |
| 2016/0256667 A1 | 9/2016 | Ribelin et al. | |
| 2017/0043066 A1 | 2/2017 | Laub | |
| 2018/0272106 A1 | 9/2018 | Funk et al. | |
| 2018/0272107 A1 | 9/2018 | Ehrenreich et al. | |

FOREIGN PATENT DOCUMENTS

| | | | |
|---|---|---|---|
| JP | 2007-029732 A | 2/2007 | |
| WO | WO 1996/021393 | 7/1996 | |
| WO | WO 2000/041617 | 7/2000 | |
| WO | WO 2000/049939 | 8/2000 | |
| WO | WO 2006/065949 | 6/2006 | |
| WO | WO 2006/090637 A1 | 8/2006 | |
| WO | WO 2008/097949 | 8/2008 | |
| WO | WO 2008/130077 | 10/2008 | |
| WO | WO 2008/138351 | 11/2008 | |
| WO | WO 2009/152470 | 12/2009 | |
| WO | WO 2010/065901 | 6/2010 | |
| WO | WO 2010/089154 | 8/2010 | |
| WO | WO 2010/107949 | 9/2010 | |
| WO | WO 2011/011436 | 1/2011 | |
| WO | WO 2011/030282 A1 | 3/2011 | |
| WO | WO 2012/064786 | 5/2012 | |
| WO | WO 2012/149109 | 11/2012 | |
| WO | WO 2013/174381 | 11/2013 | |
| WO | WO 2014/093472 | 6/2014 | |
| WO | WO 2016/033143 | 3/2016 | |
| WO | WO 2016089871 A1 * | 6/2016 | A61M 5/2033 |
| WO | WO 2016/178974 A1 | 11/2016 | |
| WO | WO 2017/136630 | 8/2017 | |
| WO | WO 2018/175529 A1 | 9/2018 | |
| WO | WO 2018/175590 A1 | 9/2018 | |

OTHER PUBLICATIONS

Office Action for U.S. Appl. No. 13/456,900, dated Nov. 2, 2012, 6 pages.
International Search Report and Written Opinion for International Application No. PCT/US2012/035122, dated Feb. 14, 2014.
International Search Report and Written Opinion for International Application No. PCT/US2015/046863, dated Dec. 21, 2015.
Supplementary European Search Report for European Application No. EP 12776089.0, dated May 13, 2015, 7 pgs.
Office Action for Chinese Patent Application No. 201280029672.2, dated May 26, 2015, 21 pgs.
Office Action for U.S. Appl. No. 13/234,857, dated Apr. 16, 2015, 17 pgs.
Office Action for U.S. Appl. No. 13/758,585, dated Jun. 10, 2015, 20 pgs.
Office Action for U.S. Appl. No. 13/758,585, dated Oct. 30, 2015, 14 pgs.
Office Action for U.S. Appl. No. 13/758,585, dated May 16, 2016, 8 pages.
Office Action for Japanese Patent Application No. 2014-508539, dated Feb. 26, 2016, 4 pgs.
Office Action for Japanese Patent Application No. 2014-508539, dated Nov. 1, 2016, 6 pgs.
Office Action for Russian Patent Application No. 2013152251, dated Feb. 24, 2016, 6 pgs.
Office Action for U.S. Appl. No. 15/199,290, dated Dec. 7, 2016, 30 pgs.
International Search Report and Written Opinion from PCT/US2010/042635, dated Feb. 25, 2011.
International Search Report and Written Opinion for International Application No. PCT/US2017/016359, dated Jun. 26, 2017, 13 pages.
Office Action for U.S. Appl. No. 14/468,826, dated Oct. 26, 2017, 7 pages.
Office Action for U.S. Appl. No. 15/680,952, dated Dec. 6, 2017, 27 pages.
Notice of Preliminary Rejection for Korean Patent Application No. 10-2013-7030879, dated Feb. 6, 2018, 11 pages.
Himberger Jr., "Accuracy of drawing blood through infusing intravenous lines," 2001 [retrieved on Mar. 16, 2011] Retrieved from the Internet <URL: <http://www.ncbi.nlm.nih.gov/pubmed/?term=Accuracy%20of%20drawing%20blood%20through%20infusing%20intravenous%20lines>.
Cox, et al. "Blood Samples Drawn from IV Catheters Have Less Hemolysis When 5-mL (vs 10-mL) Collection Tubes Are Used," J Emerg Nurs. Dec. 2004;30(6):529-33. [retrieved on Mar. 16, 2011] Retrieved from the Internet <URL: http://www.jenonline.org/article/S0099-1767(04)00634-8/fulltext>, 2 pgs.
Jagger, et al., "Drawing Venous Blood With Syringes: A Risky Use of Injection Equipment," Advances in Exposure Prevention, vol. 5, No. 3, 2000, 3 pgs.
WHO guidelines on drawing blood: best practices in phlebotomy, © World Health Organization 2010, 125 pgs.
"Connect and Protect with BD Diagnostics—Preanalytical Systems," BD Vacutainer®, Luer-Lok™, Access Device, 2 pgs, 2006.
"Needleless IV Access Devices," BD Q-Syte™, Luer Access Split-Septum, 2007, 1 pg.
"Evidence-Based Practice (EBP) Guideline Drawing Labs from Peripheral IV Sites," Nursing Research Council of United Hospital—Developed Apr. 2004; Revised Mar. 2009, 3 pgs.
Frey, "Drawing Blood Samples From Vascular Access Devices: Evidence-based Practice," Journal of Infusion Nursing: Sep./Oct. 2003, vol. 26, Issue 5, pp. 285-293, Article: CE, Abstract, [retrieved on Mar. 16, 2011], 1 pg.
"Blood Sampling Hemolysis Study for the MaxPlus™ Positive Flow Connector," Maximus Medical Products, Inc. © 2003, 1 pg.
"Vascular Access Procedures," Vascular Access Procedures, [retrieved on Mar. 16, 2011] Retrieved from the Internet <URL: http://www.radiologyinfo.org/en/info.cfm?pg=vasc_access> 7 pgs.
International Search Report and Written Opinion from International Application No. PCT/US2018/023479, dated Aug. 3, 2018, 10 pages.
International Search Report and Written Opinion from International Application No. PCT/US2018/023575, dated Aug. 8, 2018, 10 pages.
Office Action for Japanese Patent Application No. 2017-038135, dated Feb. 14, 2018, 9 pages, and English translation.

* cited by examiner

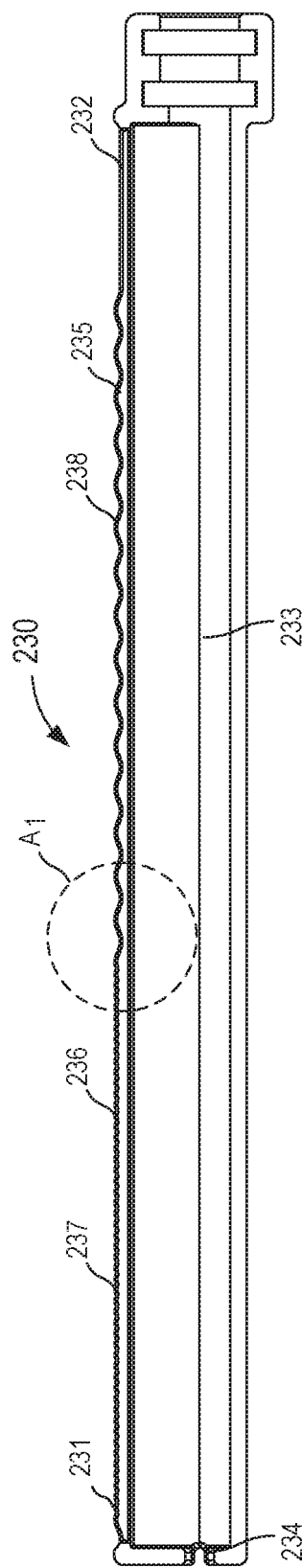
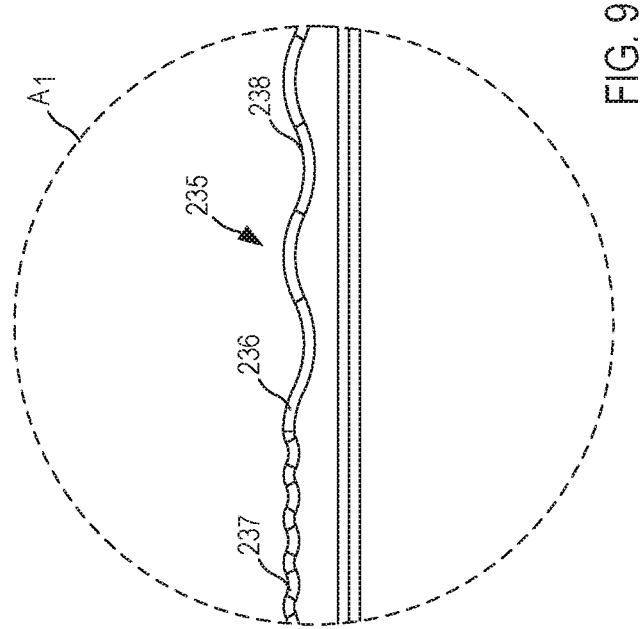
FIG. 8
FIG. 9

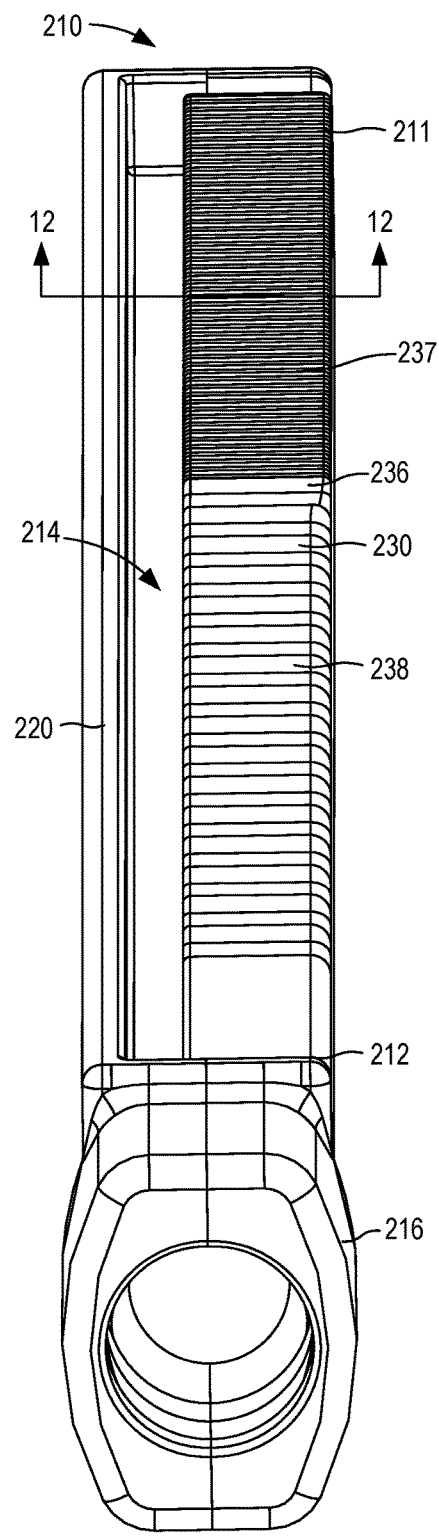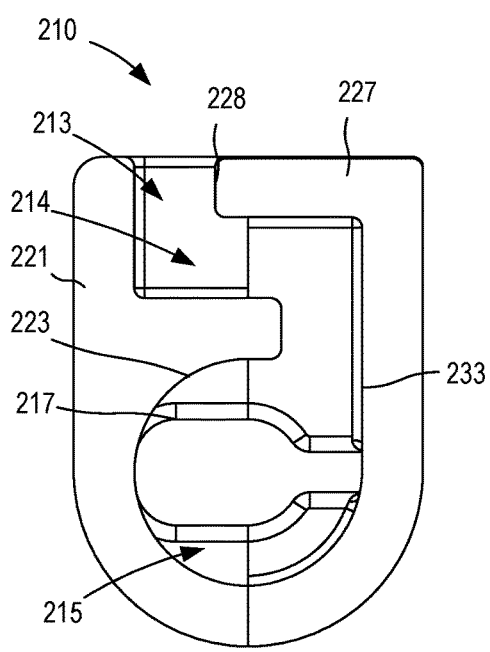
FIG. 11
FIG. 12

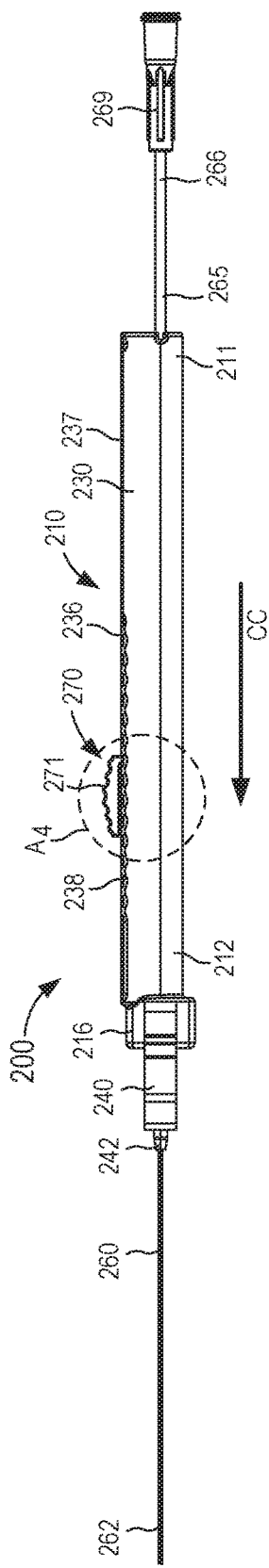
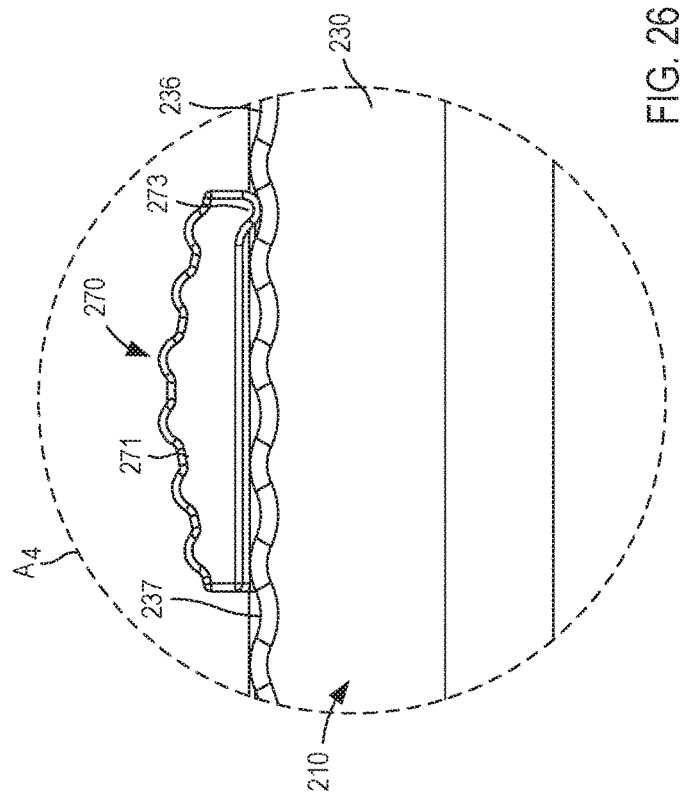
FIG. 25
FIG. 26

10

```
┌─────────────────────────────────────────────────────────────┐
│ Couple, to an indwelling peripheral intravenous line, a lock of a fluid │
│ transfer device having an introducer coupled to the lock, a catheter │
│ movably disposed in the introducer, and an actuator coupled to the │
│ catheter and in contact with an outer surface of the introducer │
│                              11                             │
└─────────────────────────────────────────────────────────────┘
                              ↓
┌─────────────────────────────────────────────────────────────┐
│ Move the actuator relative to the introducer to advance the catheter from │
│ a first position, in which the catheter is disposed within at least one of an │
│ inner volume of the introducer or the lock, toward a second position │
│                              12                             │
└─────────────────────────────────────────────────────────────┘
                              ↓
┌─────────────────────────────────────────────────────────────┐
│ Provide, to a user, an indication associated with a position of a distal end │
│ portion of the catheter as the actuator moves the catheter from the first │
│              position toward the second position            │
│                              13                             │
└─────────────────────────────────────────────────────────────┘
                              ↓
┌─────────────────────────────────────────────────────────────┐
│ Place the catheter in the second position based on the indication such │
│ that the distal end portion of the catheter is disposed beyond at least a │
│              portion of the peripheral intravenous line     │
│                              14                             │
└─────────────────────────────────────────────────────────────┘
```

FIG. 30

DEVICES AND METHODS FOR FLUID TRANSFER THROUGH A PLACED PERIPHERAL INTRAVENOUS CATHETER

BACKGROUND

The embodiments described herein relate generally to fluid transfer medical devices. More particularly, the embodiments described herein relate to devices and methods for transferring fluid to or from a patient through a placed peripheral intravenous catheter.

The typical hospitalized patient encounters a needle every time a doctor orders a lab test. The standard procedure for blood extraction involves using a metal needle ("butterfly needle") to "stick" patients' veins in their arms or hands. Blood drawing is a manual, labor-intensive process, with the average patient requiring hours of direct skilled labor during a typical hospital stay. This needle stick is not only painful and a major source of patient dissatisfaction, but the nurses or specialized blood drawing personnel (phlebotomists) often have difficulty finding the vein in approximately 10-15% of patients, resulting in multiple, painful "stick" attempts. This results in significantly higher material and labor costs (needles and tubing must be disposed of after every attempt) and increased patient pain and bruising.

The current process for drawing blood is inefficient, taking on average 7-10 minutes, and more than 21 minutes for 10% of patients. These 10% of patients are referred to as Difficult Intra-Venous Access or more commonly as "tough stick" patients. If superficial veins are not readily apparent, blood can be forced into the vein by massaging the arm from wrist to elbow, tapping the site with the index and middle finger, applying a warm, damp washcloth to the site for 5 minutes, or by lowering the extremity over the bedside to allow the veins to fill. Each of these methods is time consuming and therefore costly.

Peripheral IV catheters (PIVs) are inserted into most patients while they are hospitalized and used for infusing fluids and medications. However, they are not designed for blood extractions. The failure rates for aspiration reach 20-50% when PIVs have been left inserted for more than a day. Blood extracted from PIVs is often hemolyzed, defined as the rupture of red blood cells and the release of their contents into surrounding fluid, resulting in a discarded sample and need to repeat the blood collection.

Several barriers can contribute to the shortcomings of extracting blood through a PIV. First, most catheters are formed from a soft bio-reactive polymer, the use of this material has led to a potential narrowing or collapse of the catheter as the negative pressure is applied for aspiration. Another barrier is that longer indwelling times can increase debris (e.g., fibrin/platelet clots) that builds up on the tip of the catheter and within the lumen of the catheter and/or PIV. Similarly, such debris can at least partially occlude the lumen of the vein within which the PIV is placed. In some instances, this debris (e.g., fibrin/platelet clots) around the PIV can lead to reduced blood flow within portions of the vein surrounding the inserted PIV (e.g., both upstream and downstream), which in turn, results in improper and/or inefficient aspiration. Another barrier is attributed to a "suction cup" effect, wherein the negative pressure created by aspiration through the catheter and the possible curved path of a vein result in the tip of the catheter adhering to the wall of the vein. As the negative pressure increases the vein can rupture resulting in "blowing the vein", which is a concern for phlebotomists during aspiration through a PIV.

Thus, a need exists for an improved system and method for phlebotomy through a peripheral intravenous catheter.

SUMMARY

Devices and methods for transferring fluid to or from a patient through a placed peripheral intravenous catheter are described herein. In some embodiments, an apparatus includes a catheter, an introducer, and an actuator. The catheter has a proximal end portion and a distal end portion and defines a lumen extending through the proximal end portion and the distal end portion. The introducer has a proximal end portion and a distal end portion configured to be coupled to a peripheral intravenous line. The introducer defines an inner volume having a tortuous cross-sectional shape such that an axis defined by a first portion of the inner volume is parallel to, and offset from, an axis defined by a second portion of the inner volume. The second portion of the inner volume movably receives the catheter. The actuator includes a first portion that is movably disposed in the first portion of the inner volume and a second portion that is movably disposed in the second portion of the inner volume. The second portion of the actuator is coupled to the catheter. The actuator is configured to move relative to the introducer to move the catheter between a first position, in which the catheter is disposed within the introducer, and a second position, in which the distal end portion of the catheter is disposed beyond the distal end portion of the introducer such that at least a portion of the catheter is disposed within the peripheral intravenous line when the introducer is coupled thereto.

BRIEF DESCRIPTION OF THE DRAWINGS

FIG. 8 is a side view of the second member illustrated in FIG. 7.

FIG. 9 is an enlarged view of a portion of the second member identified in FIG. 8 by the region A1.

FIG. 11 is a front perspective view of the introducer illustrated in FIG. 10.

FIG. 12 is a cross-sectional view of the introducer taken along the line 12-12 in FIG. 11.

FIG. 25 is a side view of the fluid transfer device of FIG. 3 as the fluid transfer device is being transitioned from the first configuration to a second configuration.

FIG. 26 is an enlarged view of a portion of the fluid transfer device identified by the region A4 in FIG. 24.

FIG. 30 is a flowchart illustrating a method of using a fluid transfer device according to an embodiment.

DETAILED DESCRIPTION

Figure 1:
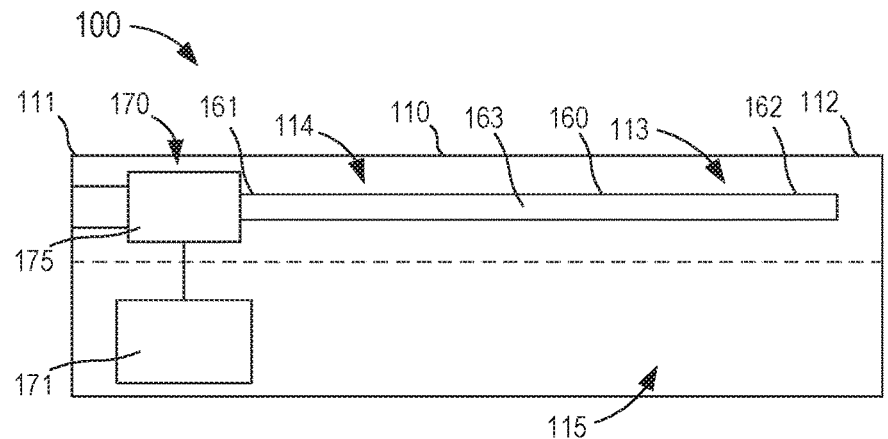
FIGS. 1 and 2 are schematic illustrations of a fluid transfer device in a first configuration and a second configuration, respectively, according to an embodiment.

Devices and methods for transferring fluid to or from a patient through a placed peripheral intravenous catheter are described herein. In some embodiments, an apparatus includes a catheter, an introducer, and an actuator. The catheter has a proximal end portion and a distal end portion and defines a lumen extending through the proximal end portion and the distal end portion. The introducer has a proximal end portion and a distal end portion configured to be coupled to a peripheral intravenous line. The introducer defines an inner volume having a tortuous cross-sectional shape such that an axis defined by a first portion of the inner volume is parallel to, and offset from, an axis defined by a second portion of the inner volume. The second portion of the inner volume movably receives the catheter. The actuator includes a first portion that is movably disposed in the first portion of the inner volume and a second portion that is movably disposed in the second portion of the inner volume. The second portion of the actuator is coupled to the catheter. The actuator is configured to move relative to the introducer to move the catheter between a first position, in which the catheter is disposed within the introducer, and a second position, in which the distal end portion of the catheter is disposed beyond the distal end portion of the introducer such that at least a portion of the catheter is disposed within the peripheral intravenous line when the introducer is coupled thereto.

In some embodiments, an apparatus includes a catheter, an introducer, an actuator, and a lock. The catheter has a proximal end portion and a distal end portion and defines a lumen extending through the proximal end portion and the distal end portion. The introducer has a proximal end portion and a distal end portion and defines an inner volume that movably receives the catheter. The actuator has a first portion disposed outside of the inner volume and a second portion disposed within the inner volume. The second portion of the actuator is coupled to the catheter. The actuator is configured to move relative to the introducer to move the catheter between a first position and a second position. The lock is coupled to the distal end portion of the introducer. The lock has a proboscis and defines a lumen extending through the proboscis. The lock is configured to be coupled to a peripheral intravenous line such that the proboscis extends through a lumen defined by the peripheral intravenous line when the lock is coupled thereto. The lumen of the proboscis receives a portion of the catheter as the catheter is moved from the first position, in which the catheter is disposed within the inner volume of the introducer, to the second position, in which the distal end portion of the catheter extends beyond the peripheral intravenous line when the lock is coupled thereto. An inner surface of the proboscis is configured to guide the catheter as the catheter is moved from the first position to the second position.

In some embodiments, an apparatus includes a catheter, an introducer, and an actuator. The catheter has a proximal end portion and a distal end portion and defines a lumen extending through the proximal end portion and the distal end portion. The introducer has a first member and a second member coupled to the first member. The second member has an outer surface forming a plurality of ribs. The first member and the second member collectively define an inner volume and a slot in communication with the inner volume. The inner volume receives the catheter. A distal end portion of the introducer configured to be coupled to a peripheral intravenous line. The actuator is operatively coupled to the introducer such that a first portion of the actuator is disposed outside of the inner volume and a second portion of the actuator extends through the slot and disposed in the inner volume. The first portion of the actuator includes a surface that is in contact with the outer surface of the second member. The second portion of the actuator is coupled to the catheter. The actuator is configured to move relative to the introducer to move the catheter between a first position, in which the catheter is disposed within the introducer, and a second position, in which the distal end portion of the catheter is disposed beyond the peripheral intravenous line when the introducer is coupled to the peripheral intravenous line. The surface of the first portion of the actuator moves along the plurality of ribs as the actuator moves the catheter between the first position and the second position to provide, to a user, a haptic feedback associated with a position of the distal end portion of the catheter.

In some embodiments, a method includes coupling a lock of a fluid transfer device to an indwelling peripheral intravenous line. The fluid transfer device includes an introducer having a distal end portion coupled to the lock, a catheter movably disposed in an inner volume defined by the introducer, and an actuator. The actuator extends through a slot defined by the introducer such that a first portion of the actuator is disposed outside of the inner volume and in contact with an outer surface of the introducer and a second portion of the actuator is disposed within the inner volume of the introducer and coupled to the catheter. The actuator is moved relative to the introducer to advance the catheter from a first position, in which the catheter is disposed within at least one of the inner volume or the lock, toward a second position. An indication associated with a position of a distal end portion of the catheter as the actuator moves the catheter from the first position toward the second position is provided to a user. The indication is in the form of a haptic output produced by a surface of the actuator being moved along a plurality of ribs included on the outer surface of the introducer. The catheter is placed in the second position based on the indication associated with the distal end portion of the catheter. The distal end portion of the catheter is disposed beyond at least a portion of the peripheral intravenous line when the catheter is in the second position.

As used herein, the terms "catheter" and "cannula" are used interchangeably to describe an element configured to define a passageway for moving a bodily fluid from a first location to a second location (e.g., a fluid passageway to move a bodily fluid out of the body). While cannulas can be configured to receive a trocar, a guide wire, or an introducer to deliver the cannula to a volume inside the body of a patient, the cannulas referred to herein need not include or receive a trocar, guide wire, or introducer.

As used in this specification, the terms "Y-adapter" and "T-adapter" are used to refer to a dual port IV extension set. In this manner, the terms "Y-adapter" and "T-adapter" generally describe an overall shape of the dual port IV extension set. For example, as used herein, a Y-adapter is substantially "Y" shaped including a single port at a first end and two ports angularly disposed at a second end. Furthermore, the terms "Y-adapter" and "T-adapter" are included by way of example only and not limitation. For example, in some embodiments, an apparatus can include a single port IV extension set (e.g., a single port adapter) or a multi-port IV extension set (e.g., an adapter with more than two ports).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "stiffness" relates to an object's resistance to deflection, deformation, and/or displacement by an applied force. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness is an extensive property of the object being described, and thus is dependent upon the material from which the object is formed as well as certain physical characteristics of the object (e.g., shape and boundary conditions). For example, the stiffness of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be increased, for example, by introducing into the object and/or constructing the object of a material having a high modulus of elasticity.

Similarly, a material's hardness is an intensive property of the constituent material and describes the measure of how resistant the material is to various kinds of permanent shape change when a force is applied. In discussing the hardness and the subsequent effect on the stiffness of a catheter, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 20 Shore D. Therefore, according to the Shore durometer scale, the second material is harder and thus, more stiff than the first material.

Figure 2:
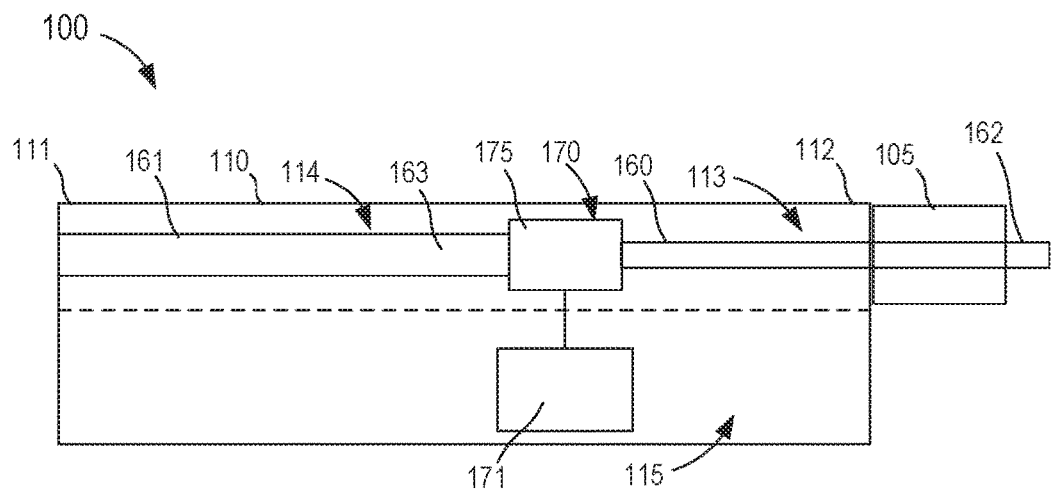

FIGS. 1 and 2 are schematic illustrations of a fluid transfer device 100 for phlebotomy through a peripheral intravenous line or catheter in a first configuration and second configuration, respectively, according to an embodiment. The fluid transfer device 100 (also referred to herein as "transfer device") can be any suitable shape, size, and/or configuration. As described in further detail herein, the transfer device 100 is configured to couple to and/or otherwise engage an indwelling peripheral intravenous catheter (PIV) 105 to transfer fluid from (e.g., aspiration of blood) and/or transfer fluid to (e.g., infusion of a drug or substance) a portion of a patient.

The transfer device 100 includes at least an introducer 110, a catheter 160 (or cannula), and an actuator 170. The introducer 110 can be any suitable configuration. For example, in some embodiments, the introducer 110 can be an elongate member having a substantially circular cross-sectional shape. In some embodiments, the shape of the introducer 110 and/or one or more features or surface finishes of at least an outer surface of the introducer 110 can be arranged to increase the ergonomics of the transfer device 100, which in some instances, can allow a user to manipulate the transfer device 100 with one hand (i.e., single-handed use).

The introducer 110 has a proximal end portion proximal end portion 111 and a distal end portion 112 and defines an inner volume 113. Although not shown in FIGS. 1 and 2, the proximal end portion 111 of the introducer 110 can include an opening or port configured to movably receive a portion of the catheter 160. As such, a first portion of the catheter 160 can be disposed within the inner volume 113 and a second portion of the catheter 160 can be disposed outside of the inner volume 113. The opening or port can be any suitable configuration. For example, in some embodiments, the opening and/or port can include a seal or the like configured to form a substantially fluid tight seal with an outer surface of the portion of the catheter 160 disposed therein. In other embodiments, the arrangement of the opening and/or port can be such that a user can place the catheter 160 in selective contact with a surface of the proximal end portion 111 defining the opening and/or port, which in turn, can clamp and/or pinch the catheter 160 to selectively obstruct a lumen of the catheter 160, as described in further detail herein with reference to specific embodiments.

The distal end portion 112 of the introducer 110 includes and/or is coupled to a lock configured to physically and fluidically couple the introducer 110 to the PIV 105 (see e.g., FIG. 2). For example, in some embodiments, the distal end portion 112 can include a coupler or the like such as a Luer Lok™ or the like configured to physically and fluidically couple to an associated coupler of the lock. In some embodiments, the lock is configured to selectively engage and/or contact the PIV 105 to couple the introducer 110 thereto. For example, in some embodiments, the shape, size, and/or arrangement of the lock is such that the lock forms three points of contact with the PIV 105. In some embodiments, such an arrangement can provide structural rigidity and/or support to the PIV 105 as a portion of the lock (e.g., a proboscis or the like) is inserted into a portion of the PIV 105, as described in further detail herein.

In some embodiments, the distal end portion 112 of the introducer 110 (and/or the lock) can include a seal or the like that can be transferred from a sealed configuration to a substantially open configuration to place at least a portion of the inner volume 113 in fluid communication with the lock. In some embodiments, the seal can include back flow prevention mechanism such as a one-way valve or the like that can allow, for example, the catheter 160 to be advanced in the distal direction therethrough while limiting and/or substantially preventing a fluid flow, outside the catheter 160, in the proximal direction through the seal.

As described above, the introducer 110 defines the inner volume 113, which extends between the proximal end portion 111 and the distal end portion 112. The inner volume 113 has and/or defines a first portion 114 configured to receive a first portion 171 of the actuator 170 and a second portion 115 configured to receive the catheter 160 and a second portion 175 of the actuator 172, as shown in FIGS. 1 and 2. More specifically, an inner surface of the introducer 110 that defines the inner volume 113 can have, for example, a tortuous cross-sectional shape (not shown in FIGS. 1 and 2) such that an axis defined by the first portion 114 of the inner volume 113 is parallel to and offset from an axis defined by the second portion 115 of the inner volume 113. In this manner, the first portion 114 of the inner volume 113 can be spaced apart from the second portion 115 of the inner volume 113 without being fluidically isolated therefrom. In some embodiments, the first portion 114 of the inner volume 113 can extend through a wall of the introducer 110. In other words, the introducer 110 can define a slot, channel, track, opening, and/or the like that is in fluid communication with the first portion 114 of the inner volume 113. Conversely, the second portion 115 of the inner volume 113 can be entirely defined and/or enclosed (at least in the circumferential direction) by the introducer 110. Moreover, in some embodiments, the tortuous cross-sectional shape of the inner volume 113 is such that the second portion 115 cannot be viewed (e.g., is out of the line of sight) via the slot or the like in fluid communication with the first portion 114 of the inner volume 113, which in turn, can limit and/or substantially prevent contamination of the catheter 160 disposed therein.

The catheter 160 of the transfer device 100 includes a proximal end portion 161 and a distal end portion 162 and defines a lumen 163 that extends through the proximal end portion 161 and the distal end portion 162. The catheter 160 is movably disposed within the second portion 115 of the inner volume 113 defined by the introducer 110 and is coupled to the actuator 170. In some embodiments, the catheter 160 can be moved (e.g., via movement of the actuator 170) between a first position and a second position to transition the transfer device 100 between the first configuration and the second configuration, respectively. More specifically, at least the distal end portion 162 of the catheter 160 is disposed within the second portion 115 of the inner volume 113 when the catheter 160 is in the first position (FIG. 1) and at least a portion of the catheter 160 extends through the PIV 105 to place a distal end of the catheter 160 in a distal position relative to a portion of the PIV 105 when the catheter 160 is in the second position (FIG. 2). Although not shown in FIGS. 1 and 2, in some embodiments, the transfer device 100 can include a secondary catheter or the like that is coupled to the actuator 170 and in fluid communication with the catheter 160. In such embodiments, the secondary catheter can be, for example, disposed in a proximal position relative to the catheter 160 and can be configured to extend through the opening and/or port defined by the proximal end portion 111 of the introducer 110. In this manner, a proximal end portion of the secondary catheter can be coupled to a fluid reservoir, fluid source, syringe, and/or the like, which in turn, places the catheter 160 in fluid communication therewith. Moreover, in embodiments including the secondary catheter, the catheter 160 can be entirely disposed within the introducer 110 when the catheter 160 is in the first position.

The catheter 160 can be any suitable shape, size, and/or configuration. For example, in some embodiments, at least a portion of the catheter 160 can have an outer diameter (e.g., between a 16-gauge and a 26-gauge) that is substantially similar to or slightly smaller than an inner diameter defined by a portion of the lock coupled to the distal end portion 112 of the introducer 110. In this manner, an inner surface of the portion of the lock can guide the catheter 160 as the catheter 160 is moved between the first position and the second position. In some embodiments, such an arrangement can limit and/or can substantially prevent bending, deforming, and/or kinking of the catheter 160 as the catheter 160 is moved between the first position and the second position. In some embodiments, the catheter 160 can have a length that is sufficient to place a distal surface of the catheter 160 in a desired position relative to a distal surface of the PIV 105 when the catheter 160 is in the second position. In other words, the length of the catheter 160 can be sufficient to define a predetermined and/or desired distance between the distal surface of the catheter 160 and the distal surface of the PIV 105 when the catheter 160 is in the second position. In some instances, placing the distal surface of the catheter 160 the predetermined and/or desired distance from the distal surface of the PIV 105 can, for example, place the distal surface of the catheter 160 in a desired position within a vein, as described in further detail herein.

The catheter 160 can be formed from any suitable material or combination of materials, which in turn, can result in the catheter 160 having any suitable stiffness or durometer. In some embodiments, at least a portion of the catheter 160 can be formed of a braided material or the like, which can change, modify, and/or alter a flexibility of the catheter 160 in response to a bending force or the like. In some embodiments, forming the catheter 160 of the braided material or the like can reduce a likelihood of kinking and/or otherwise deforming in an undesired manner. In addition, forming at least a portion of the catheter 160 of a braided material can result in a compression and/or deformation in response to a compression force exerted in a direction of a longitudinal centerline defined by the catheter 160 (e.g., an axial force or the like). In this manner, the catheter 160 can absorb a portion of force associated with, for example, impacting an obstruction or the like.

The actuator 170 of the transfer device 100 can be any suitable shape, size, and/or configuration. As described above, the actuator 170 includes the first portion 171 movably disposed within the first portion 114 of the inner volume 113 and the second portion 175 movably disposed within the second portion 115 of the inner volume 113 and coupled to the catheter 160. Although not shown in FIGS. 1 and 2, the actuator 170 can have a cross-sectional shape that is associated with and/or otherwise corresponds to the cross-sectional shape of the inner volume 113 (e.g., the tortuous cross-sectional shape). Thus, an axis defined by the first portion 171 of the actuator 170 is parallel to and offset from an axis defined by the second portion 175 of the actuator 170.

The arrangement of the actuator 170 and the introducer 110 is such that the first portion 171 extends through the slot or the like in fluid communication with the first portion 114 of the inner volume 113. As such, a first region of the first portion 171 of the actuator 170 is disposed outside of the introducer 110 and a second region of the first portion 171 of the actuator 170 is disposed in the first portion 114 of the inner volume 113. In this manner, a user can engage the first region of the first portion 171 of the actuator 170 and can move the actuator 170 relative to the introducer 110 to move the catheter 160 coupled to the second portion 175 of the actuator 170 between the first position and the second position. Although not shown in FIGS. 1 and 2, in some embodiments, the first portion 171 of the actuator 170 can include a tab, protrusion, and/or surface that is in contact with an outer surface of the introducer 110. In such embodiments, the outer surface of the introducer 110 can include, for example, a set of ribs, ridges, bumps, grooves, and/or the like along which the tab, protrusion, and/or surface of the first portion 171 advances when the actuator 170 is moved relative to the introducer 110, which in turn, produces a haptic output or feedback which can provide an indication associated with a position of the distal end portion 162 of the catheter 160 to the user.

In some embodiments, the transfer device 100 can be disposed in the first configuration prior to use (e.g., shipped, stored, prepared, etc. in the first configuration). In use, a user can manipulate the transfer device 100 to couple the introducer 110 to the indwelling PIV 105 (e.g., via the lock coupled to and/or assembled with the introducer 110). With the transfer device 100 coupled to the PIV 105, the user can engage the first portion 171 of the actuator 170 to move the actuator 170 relative to the introducer 110, which in turn, moves the catheter 160 from the first position (e.g., disposed within the introducer 110) toward the second position. In some embodiments, the arrangement of the actuator 170 and the introducer 110 is such that advancing the actuator 170 relative to the introducer 110 produces a haptic output and/or feedback configured to provide and indicator associated with position of the distal end portion 162 of the catheter 160 relative to the introducer 110 and/or the PIV 105 to the user. For example, based on the haptic feedback or the any other suitable indicator, the user can place the catheter 160 in the second position such that the distal surface of the catheter 160 extends a desired distance beyond the distal surface of the PIV 105, as described above.

With the catheter 160 in the second position (e.g., with the transfer device 100 in the second configuration shown in FIG. 2), the user can establish fluid communication between a fluid reservoir, fluid source, syringe, and/or the like and the catheter 160. For example, as described above, in some embodiments, the user can couple the secondary catheter (not shown) to the fluid reservoir, fluid source, syringe, and/or the like. Although described as establishing fluid communication between the catheter 160 and the fluid reservoir or fluid source after placing the catheter 160 in the second position, in other embodiments, the user can establish fluid communication between the catheter 160 and the fluid reservoir or fluid source prior to moving the actuator 170 relative to the introducer 110. With the catheter 160 in fluid communication with the fluid reservoir and/or fluid source, the transfer device 100 can then transfer a fluid from the patient or transfer a fluid to the patient via the catheter 160 extending through and beyond the PIV 105.

FIGS. 3-29 illustrate a fluid transfer device 200 according to another embodiment. The fluid transfer device 200 (also referred to herein as "transfer device") can be any suitable shape, size, or configuration and can be coupled to a PIV (not shown in FIGS. 3-29), for example, via a lock and/or adapter. As described in further detail herein, a user can transition the transfer device 200 from a first configuration to a second configuration to advance a catheter through an existing, placed, and/or indwelling PIV (i.e., when the transfer device 200 is coupled thereto) such that at least an end portion of the catheter is disposed in a distal position relative to the PIV. Moreover, with peripheral intravenous lines each having a shape, size, and/or configuration that can vary based on, for example, a manufacturer of the PIV and/or its intended usage, the transfer device 200 can be arranged to allow the transfer device 200 to be coupled to a PIV having any suitable configuration and subsequently, to advance at least a portion of a catheter through the PIV substantially without kinking, snagging, breaking, and/or otherwise reconfiguring the catheter in an undesirable manner. In addition, the transfer device 200 can be manipulated by a user to place a distal surface of the catheter a predetermined and/or desired distance beyond a distal surface of the PIV to be disposed within a portion of a vein that receives a substantially unobstructed flow of blood.

Figure 3:
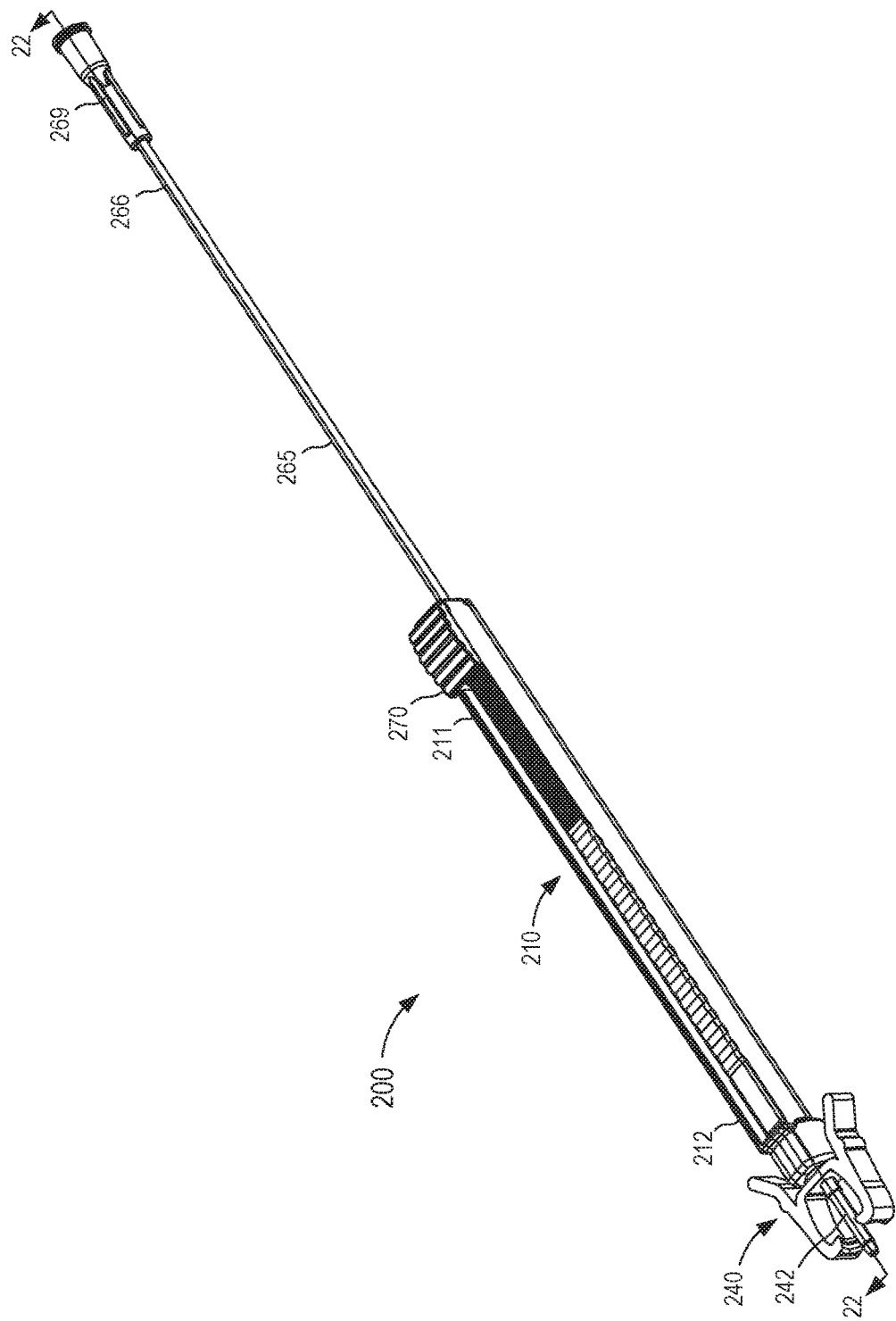
FIG. 3 is a perspective view of a fluid transfer device in a first configuration, according to an embodiment.
Figure 4:
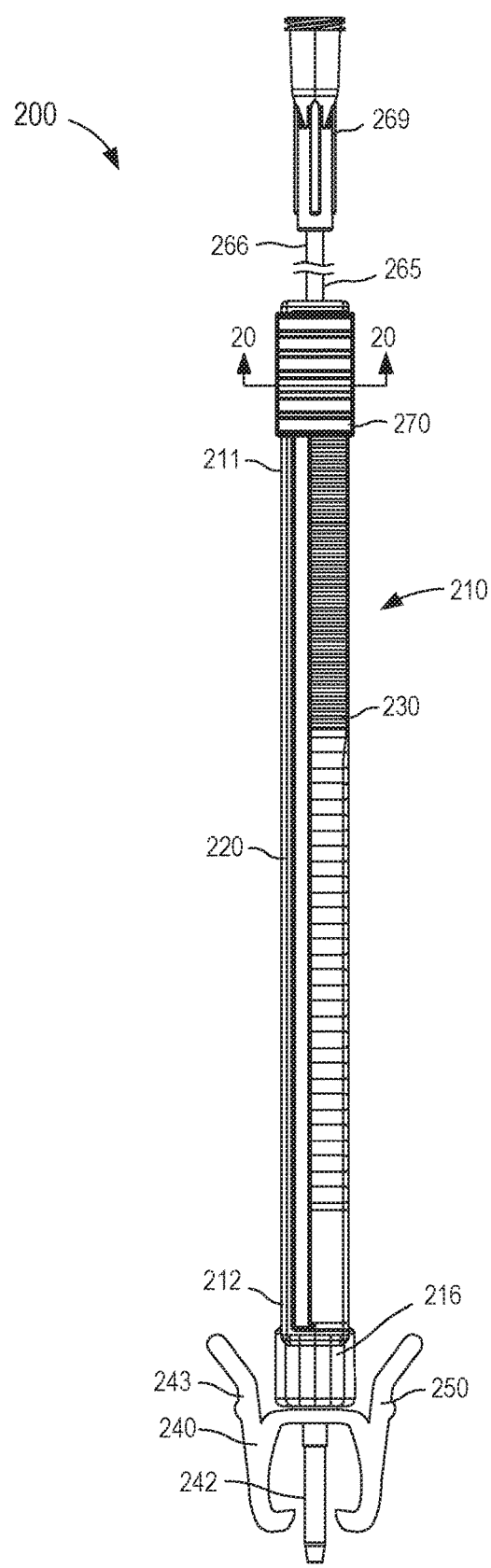
FIG. 4 is a top view of the fluid transfer device illustrated in FIG. 3.
Figure 5:
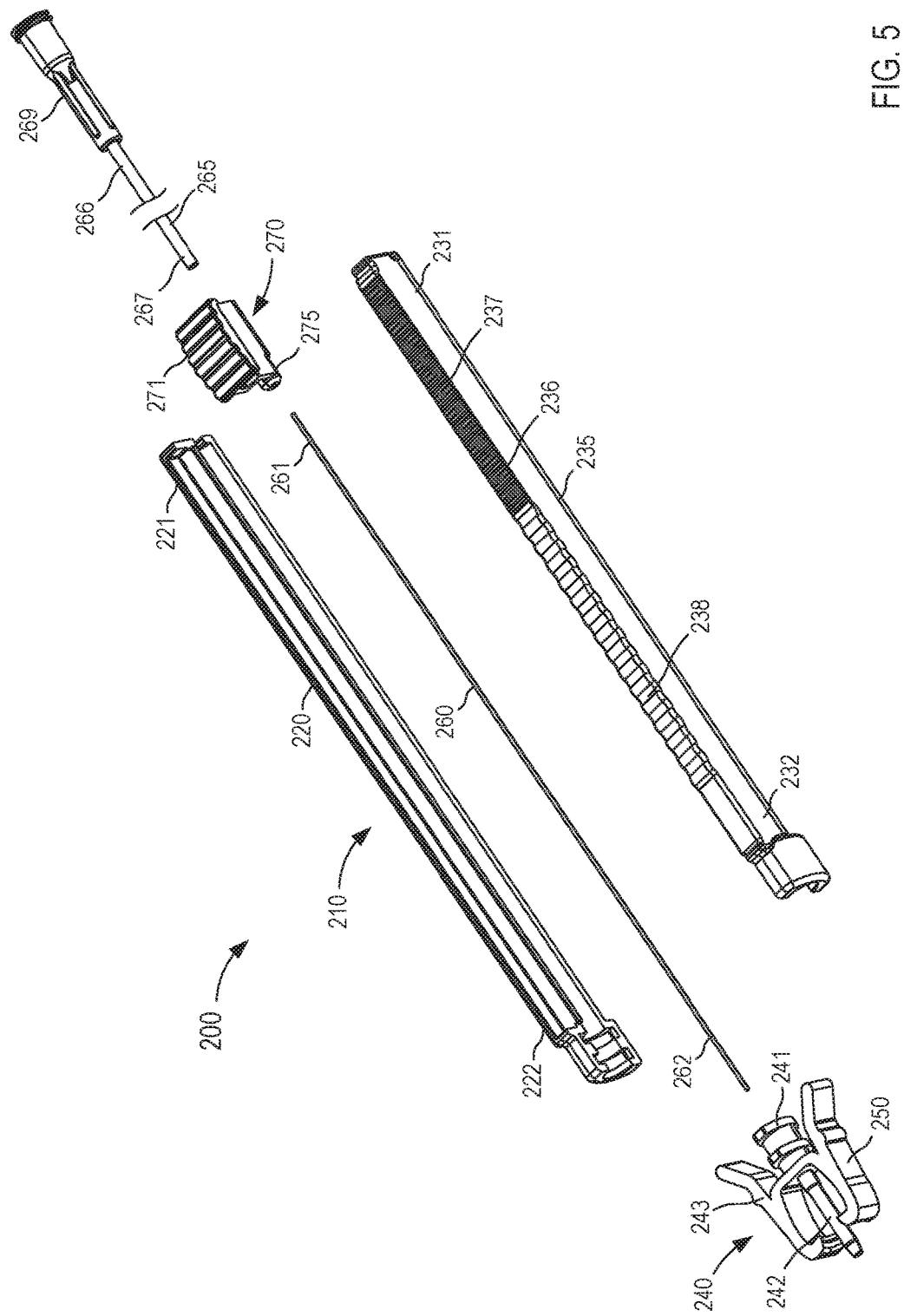
FIG. 5 is an exploded view of the fluid transfer device illustrated in FIG. 3.

As shown in FIGS. 3-5, the transfer device 200 includes an introducer 210, a lock 240, a catheter 260, a secondary catheter 265, and an actuator 270. The introducer 210 can be any suitable shape, size, or configuration. For example, in some embodiments, the introducer 210 can be an elongate member having a substantially circular cross-sectional shape. In some embodiments, the shape of the introducer 210 and/or one or more features or surface finishes of at least an outer surface of the introducer 210 can be arranged to increase the ergonomics of the transfer device 200, which in some instances, can allow a user to manipulate the transfer device 200 with one hand (i.e., single-handed use).

Figure 6:
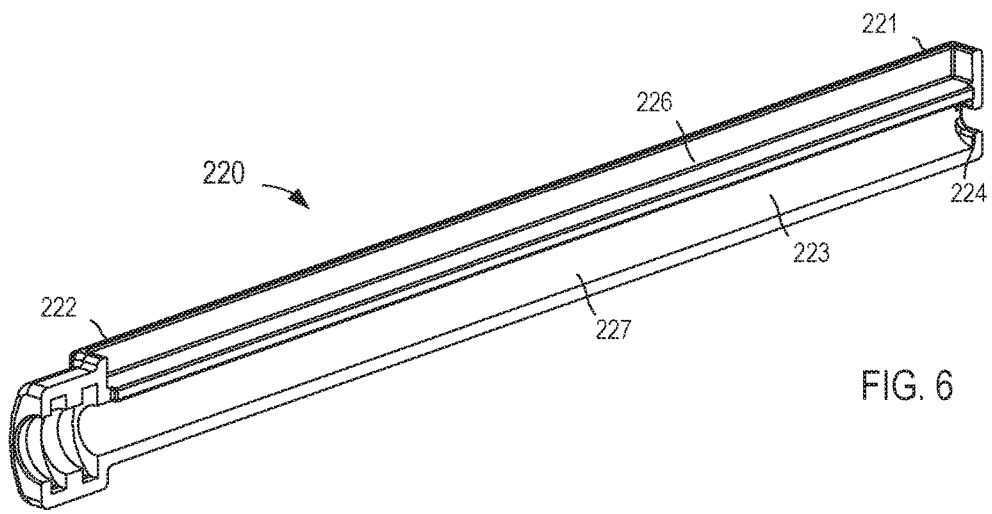
FIG. 6 is a perspective view of a first member of an introducer included in the fluid transfer device of FIG. 3.

As shown in FIGS. 5-12, the introducer 210 of the transfer device 200 includes a first member 220 and a second member 225 that are coupled to collectively form the introducer 210. As shown in FIG. 6, the first member 220 includes a proximal end portion 221, a distal end portion 222, and an inner surface 224. The inner surface 224 has a first portion 224 and a second portion 225. The proximal end portion 221 of the first member 220, and more specifically, a proximal wall of the first member 220 defines a notch 226 configured to selectively receive a portion of the secondary catheter 265, as described in further detail herein.

Figure 7:
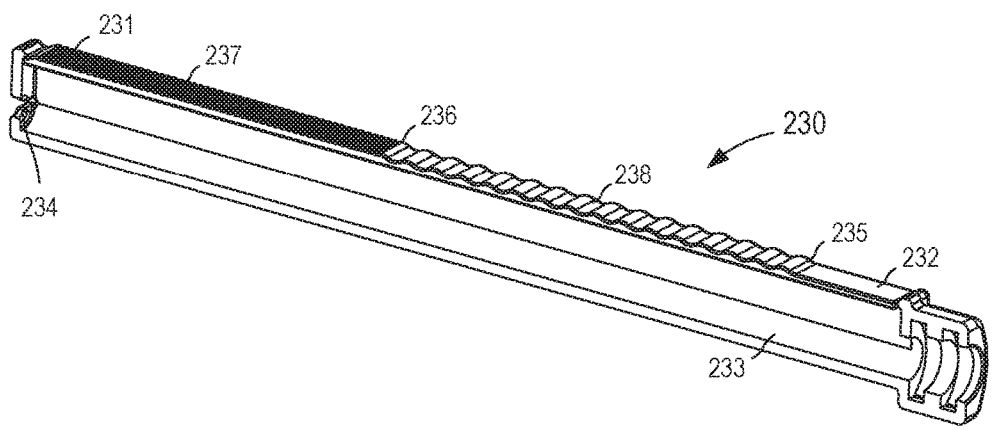
FIG. 7 is a perspective view of a second member of the introducer included in the fluid transfer device of FIG. 3.

As shown in FIGS. 7-9, the second member 230 has a proximal end portion 231, a distal end portion 232, an inner surface 233, and an outer surface 235. As described above with reference to the first member 220, the proximal end portion 231 of the second member 230, and more specifically, a proximal wall of the second member 230 defines a notch 234 configured to selectively receive a portion of the secondary catheter 265. The outer surface 235 of the second member 230 includes a set of ribs 236 distributed along a length of the second member 230. More particularly, each rib 236 extends along a width of the second member 230 and successively distributed along the length of the second member 230. In this manner, the outer surface 235 defines alternating local minima and local maxima arranged along the length of the second member 230. As described in further detail herein, a portion of the actuator 270 is configured to be advanced along the outer surface 235 forming the set of ribs 236 as a user moves the actuator 270 relative to the introducer 210, which in turn, vibrates the actuator 270 (and the catheter 260 coupled thereto). In some instances, this vibration can, for example, facilitate the advancing of the catheter 260 through a portion or the transfer device 200, a portion of the PIV, and/or a portion of the vasculature. Moreover, in some instances, the vibration can provide a user with a haptic and/or audible indicator associated with a position of the catheter 260 relative to the introducer 210 and/or PIV, as described in further detail herein.

The ribs 236 formed by the outer surface 235 of the second member 230 can be any suitable shape, size, and/or configuration. For example, as shown in FIGS. 8 and 9, the set of ribs 236 includes a first portion 237 having a first size and shape, and a second portion 238 having a second size and shape, different from the first size and shape. The first portion 237 of ribs 236 can have any suitable configuration and/or arrangement. For example, in this embodiment, each rib in the first portion 237 is substantially uniform having substantially the same size and shape. In other embodiments, each rib included in the first portion 237 can have a size and shape that is different from the remaining ribs of the first portion 237. For example, in some embodiments, the size and shape of each rib in the first portion 237 can increase from a proximal most rib having the smallest size and shape to a distal most rib having the largest size and shape. Moreover, while the ribs of the first portion 237 are shown as being substantially symmetrical, in other embodiments, each rib of the first portion 237 can be asymmetrical. For example, in some embodiments, a proximal surface of each rib can have a first pitch (e.g., angle) and a distal surface of each rib can have a second pitch that is greater than the first pitch. In some embodiments, such an asymmetric arrangement can be such that the portion of the actuator 270 moves along the outer surface 235 with a first set of characteristics when moved in a distal direction and moves along the outer surface 235 with a second set of characteristics, different from the first set of characteristics, when moved in a proximal direction. For example, in some embodiments, the portion of the actuator 270 can move along the outer surface 235 in the distal direction more freely than in the proximal direction.

Similarly, the second portion 238 of the ribs 236 can have any suitable configuration and/or arrangement. For example, in this embodiment, each rib in the second portion 238 is substantially uniform having substantially the same size and shape as the remaining ribs in the second portion 238. As shown in FIG. 9, each rib in the second portion 238 has a size and shape that is greater than the size and shape of each rib of the first portion 237. In some instances, the greater size of the ribs of the second portion 238 can result in a larger amount of vibration as the actuator 270 is moved along the outer surface 235 (as described above). In some instances, the greater size of the ribs of the second portion 238 can result in an increase in a force otherwise sufficient to move the portion of the actuator 270 along the outer surface 235. While the ribs of the second portion 238 are shown and described as being substantially uniform and having a larger size than the ribs of the first portion 237, in other embodiments, the ribs of the second portion 238 can have any of the arrangements and/or configurations described above with reference to the ribs of the first portion 237.

While the set of ribs 236 transitions from the first portion 237 to the second portion 238 at a given point along the length of the second member 230 (see e.g., FIG. 9), in other embodiments, the size and shape of each rib in the set of ribs 236 can increase from a proximal most rib of the first portion 237 having the smallest size and shape to a distal most rib of the second portion 238 having the largest size and shape. In other words, in some embodiments, the size and shape of each of rib in the set of ribs 236 can increase with each successive rib (e.g., in the distal direction). In still other embodiments, the set of ribs 236 can include more than the first portion 237 and the second portion 238. For example, in some embodiments, a second member can include a set of ribs having a first portion and a second portion having a size, shape, and configuration similar to the first portion 237 of the second member 230, and a third portion, disposed between the first portion and the second portion, having a size, shape, and configuration similar to the second portion 238 of the second member 230. That is to say, in such embodiments, the second member includes a proximal portion of ribs and a distal end portion of ribs that are smaller than a medial portion of ribs disposed therebetween. In some embodiments, the arrangement of the set of ribs 236 of the second member 230 can be such that a proximal most rib and a distal most rib are larger and/or otherwise have a shape that operable to at least temporarily maintain the portion of the actuator 270 in a proximal position relative to the proximal most rib and a distal position relative to the distal most rib, respectively.

While the set of ribs 236 are shown as being formed only by the outer surface 235 of the second member 230, in other embodiments, the first member 220 can include an outer surface that forms a set of ribs. In such embodiments, the set of ribs of the first member 220 can be and/or can have any of the configurations and/or arrangements described above with reference to the set of ribs 236 of the second member 230. In some embodiments, the ribs of the first member 220 can be offset from the ribs 236 of the second member 230. For example, in some embodiments, the ribs of the first member 220 can have alternating local minima and local maxima (as described above with reference to the ribs 236) that are distributed along a length of the first member 220 such that the local minima and local maxima of the ribs of the first member 220 are aligned with the local maxima and local minima, respectively, of the ribs 236 of the second member 230 (e.g., offset along a length of the introducer 210). In other embodiments, the ribs of the first member 220 can be in varying positions relative to the ribs 236 of the second member 230. In this manner, the introducer 210 can provide a variable arrangement of ribs that can provide, for example, haptic feedback as the actuator 270 is moved relative to the introducer 210.

Figure 10:
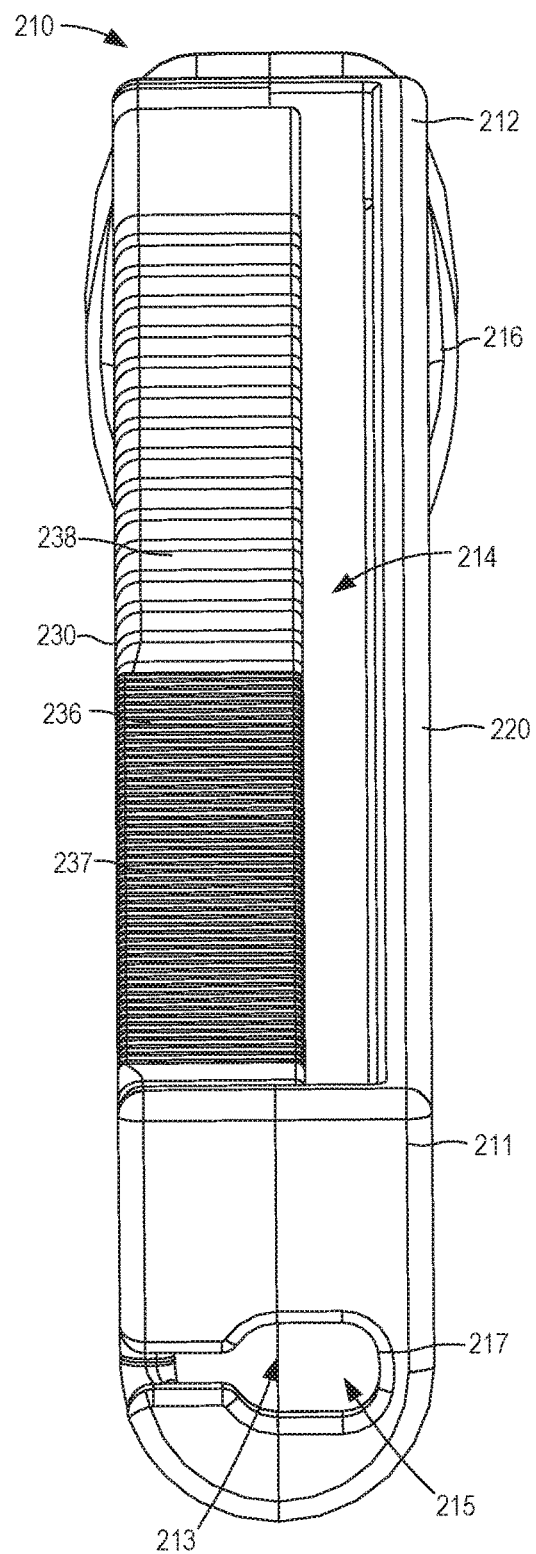
FIG. 10 is a rear perspective view of the introducer formed by coupling the first member illustrated in FIG. 6 to the second member illustrated in FIG. 7.

As shown in FIGS. 10-12, the first member 220 is configured to be coupled to the second member 230 to collectively form the introducer 210. For example, in some embodiments, the first member 220 and the second member 230 can be coupled via ultrasonic welding, an adhesive, a mechanical fastener, one or more tabs, snaps, pins, and/or the like to form the introducer 210. In some embodiments, coupling the first member 220 to the second member 230 (e.g., during a manufacturing process) to form the introducer 210 can facilitate and/or simplify one or more manufacturing processes. For example, in some embodiments, forming the introducer 210 from the first member 220 and the second member 230 can reduce undesirable variations in the shape and/or size of the inner surface 223 and 233 (e.g., due to draft angles and/or manufacturing tolerances) during manufacturing, which in some instances, can reduce a likelihood of kinks, bends, and/or deformations of the catheter 260 during use of the transfer device 200. In some embodiments, forming the introducer 210 from the first member 220 and the second member 230 can allow at least the inner surface 223 of the first member 220 to form a tortuous shape that would otherwise present challenges when manufacturing the introducer 210 from a single workpiece.

In other embodiments, a first member 220 can be monolithically formed (e.g., via injection molding and/or any other suitable manufacturing process). That is to say, the first member 220 can be formed from a single workpiece or the like rather than two workpieces, namely, the first member 220 and the second member 230. Thus, when referring to features of the first member 220, such features can be formed and/or defined by the first member 220, formed and/or defined by the second member 230, collectively formed and/or defined by the first member 220 and the second member 230, or, when the introducer 210 is formed from a single workpiece, formed and/or defined by a corresponding portion of the introducer 210.

The first member 220 and the second member 230 collectively form a proximal end portion 211 and a distal end portion 212 of the introducer 210 and collectively define an inner volume 213 of the introducer 210. As shown in FIG. 10, the proximal end portion 211 of the introducer 210 defines an opening 217. Specifically, the opening 217 is collectively formed and/or defined by the notch 226 of the first member 220 and the notch 234 of the second member 230. The arrangement of the proximal end portion 211 is such that a portion of the opening 217 defined by the notch 226 of the first member 220 has a first size and/or shape and a portion of the opening 217 defined by the notch 234 of the second member 230 has a second size and/or shape that is less than the first size and/or shape. In other words, a portion of the opening 217 is constricted, pinched, obstructed, and/or otherwise reduced. As described in further detail herein, the opening 217 is configured to receive a portion of the secondary catheter 265, which can be moved within the opening 217 from the larger portion of the opening 217 to the reduced portion of the opening 217 (e.g., the portion formed by the notch 234 of the second member 230) to obstruct, pinch, and/or clamp the secondary catheter 265.

As shown in FIG. 11, the distal end portion 212 of the introducer 210 includes and/or otherwise forms a coupler 216. In other words, the distal end portion 222 of the first member 220 and the distal end portion 232 of the second member 230 collectively form the coupler 216 at the distal end portion 212 of the introducer 210. The coupler 216 can be any suitable shape, size, and/or configuration. For example, in this embodiments, the coupler 216 forms a set of threads, which can form a threaded coupling with an associated threaded portion of the lock 240, as described in further detail herein. Although not shown in FIG. 11, the distal end portion 211 of the introducer 210 can include and/or can be configured to receive a seal that can selectively seal and/or fluidically isolate the inner volume 213 of the introducer 210 (at least from an open portion of the coupler 216). In use, the seal can be transitioned from a sealed or closed configuration to an open configuration to allow, for example, a portion of the catheter 260 to pass therethrough. In some embodiments, the seal can contact an outer surface of the catheter 260 to define a seal therebetween that is operable to limit and/or substantially prevent a back flow of fluid between the outer surface of the cannula and the seal.

The seal can be any suitable type of seal. For example, in some embodiments, the seal can be an O-ring, a one-way valve, a diaphragm, a self-healing diaphragm, a check valve, a single crack valve, and/or any other suitable seal or valve member. In some embodiments, the seal is configured to define and/or otherwise have a predetermined "cracking" pressure. That is to say, in some embodiments, the seal can be configured to transition from a closed and/or sealed configuration to a substantially open configuration in response to an increase in pressure, for example, within the introducer 210. In some embodiments, the seal can be a positive pressure seal or the like. In other embodiments, the seal can be a fluid seal such as a saline lock or the like. Although not shown in FIGS. 5-12, in some embodiments, the introducer 210 can include a device, mechanism, assembly, and/or the like, which can be manipulated to increase a pressure (e.g., via air or other suitable fluid or liquid) within the introducer 210 to transition the seal from the closed configuration to the open configuration. For example, the introducer 210 can include and/or can be coupled to a bulb, pump, a syringe, a fluid source, a mechanical actuator, an electric actuator, and/or the like. In other embodiments, the seal can be any other suitable configuration.

The inner surface 223 of the first member 220 and the inner surface 233 of the second member 230 collectively define the inner volume 213 of the introducer 210. As shown in FIG. 12, the arrangement of the inner surfaces 223 and 233 is such that the inner volume 213 has and/or defines a tortuous cross-sectional shape. For example, the inner volume 213 can have a substantially S-shaped or an at least partially S-shaped cross-sectional shape. More specifically, the inner surface 223 of the first member 220 includes and/or forms a ridge, tab, flange, protrusion, and/or wall configured to separate the first portion 224 of the inner surface 223 from the second portion 225 of the inner surface 223. Thus, the tortuous cross-sectional shape of the inner volume 213 forms and/or defines a first portion 214 of the inner volume 213 and a second portion 215 of the inner volume 213. In this manner, the first portion 214 of the inner volume 213 is spaced apart from the second portion 215 of the inner volume 213 without being fluidically isolated therefrom. In other words, the first portion 214 of the inner volume 213 defines an axis that is parallel to and offset from an axis defined by the second portion 215 of the inner volume 213.

As shown in FIG. 12, the first portion 214 of the inner volume 213 extend through a wall of the introducer 210. Similarly stated, the introducer 210 defines (e.g., the first member 220 and the second member 230 collectively define) a slot, channel, track, opening, and/or the like (referred to herein as slot 228) that is in fluid communication with the first portion 214 of the inner volume 213. Conversely, the second portion 215 of the inner volume 213 is entirely defined and/or enclosed (at least in the circumferential direction) by the introducer 210. The tortuous cross-sectional shape of the inner volume 213 is such that the second portion 215 cannot be viewed (e.g., is out of the line of sight) via the slot 228 (in fluid communication with the first portion 214 of the inner volume 213), which in turn, can limit and/or substantially prevent contamination of the catheter 260 disposed therein.

In this embodiment, the second portion 215 of the inner volume 213 is substantially aligned with, for example, a portion of the opening 217 and a portion of an opening defined by the coupler 216. Moreover, the second portion 215 of the inner volume 213 is configured to be substantially aligned with the lock 240 when the lock is coupled to the coupler 216 of the introducer 210. In other words, the axis defined by the second portion 215 of the inner volume 213 is substantially co-axial with an axis defined by a portion of the lock 240, as described in further detail herein. In this manner, the second portion 215 of the inner volume 213 can movably receive, for example, a portion of the actuator 270 and a portion of the catheter 260. Thus, the actuator 270 can be moved relative to the introducer 210 to move the catheter 260 between a first position, in which the catheter 260 is entirely disposed within the second portion 215 of the inner volume 213, and a second position, in which at least a portion of the catheter 260 extends outside of the second portion 215 of the inner volume 213 and distal to the introducer 210, as described in further detail herein.

Figure 13:
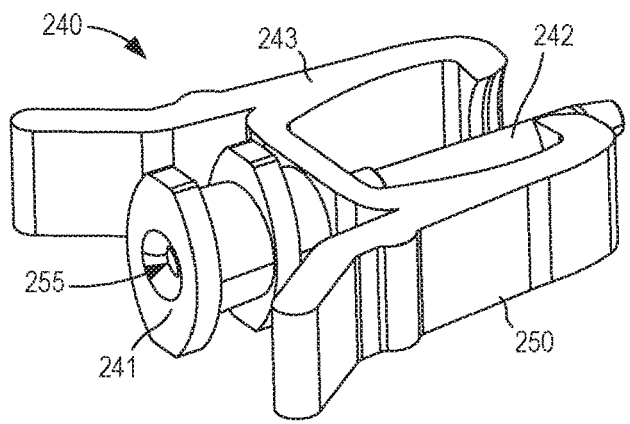
FIGS. 13 and 14 are a rear perspective view and a top view, respectively, of a lock included in the fluid transfer device of FIG. 3.
Figure 14:
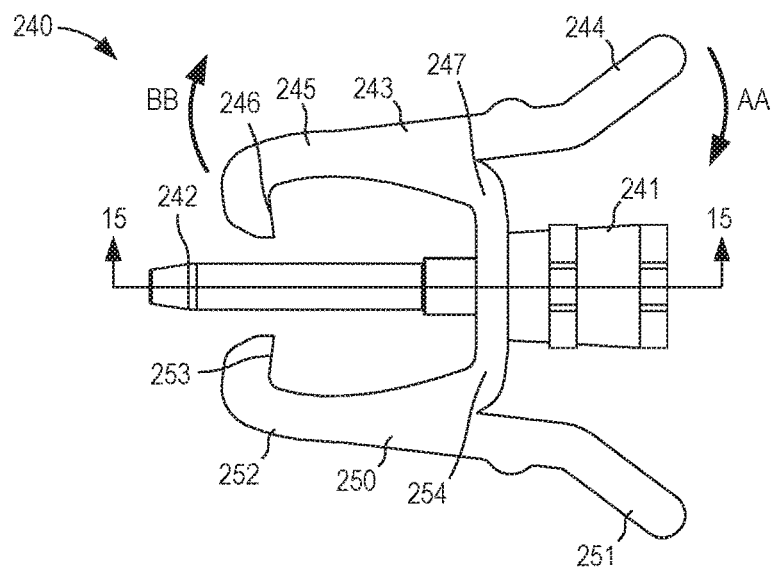
Figure 15:
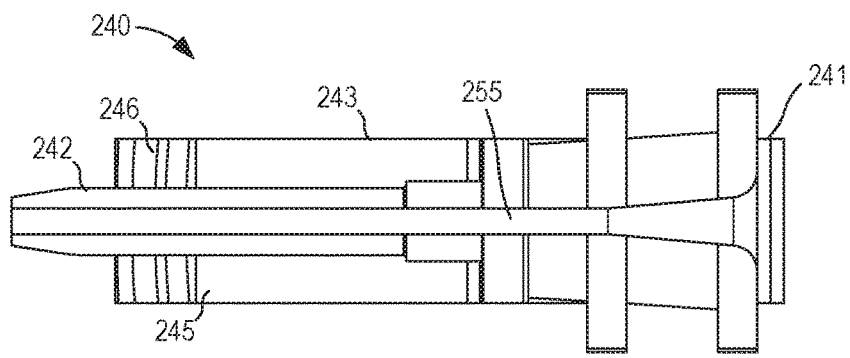
FIG. 15 is a cross-sectional view of the lock taken along the line 15-15 in FIG. 14.

The lock 240 of the transfer device 200 can be any suitable shape, size, and/or configuration. As described above, the lock 240 is configured to be physically and fluidically coupled to the introducer 210 and configured to couple the introducer 210 to the PIV and/or any suitable intermediate device or adapter coupled to the PIV. The lock 240 has a coupler 241, a proboscis 242, a first arm 243, and a second arm 250, as shown in FIGS. 13-15. In addition, the lock 240 defines a lumen 255 extending through the coupler 241 and the proboscis 242. The coupler 241 is configured to couple the lock 240 to the coupler 216 of the introducer 210. Specifically, in this embodiment, the coupler 241 includes and/or forms one or more protrusions configured to selectively engage the threads defined and/or formed by the coupler 216 of the introducer 210, thereby forming a threaded coupling.

The proboscis 242 extends from the coupler 246 and is disposed between the first arm 243 and the second arm 250. The proboscis 242 can be any suitable shape, size, and/or configuration. In some embodiments, the configuration of the proboscis 242 can be associated with or at least partially based on a size and/or shape of the PIV, a size and/or shape of an adapter (e.g., an extension set, a Y-adapter, a T-adapter, or the like), or a collective size and/or shape of the PIV and the adapter. For example, in some embodiments, the proboscis 242 can have a length that is sufficient to extend through at least a portion of the PIV (or adapter). In embodiments including an adapter coupled to the PIV, the proboscis 242 can be sufficiently long to extend through the adapter and at least partially into or through the PIV. In some embodiments, the proboscis 242 can be sufficiently long to extend through an adapter and the PIV such that at least a portion of the proboscis 242 is distal to the PIV. Moreover, the proboscis 242 can have an outer diameter that is similar to or slightly smaller than an inner diameter of a portion of the PIV and/or adapter coupled thereto. For example, in some embodiments, an outer surface of the proboscis 242 can be in contact with an inner surface of the PIV when the proboscis 242 is disposed therein. In this manner, the proboscis 242 can provide structural support to at least a portion of the PIV within which the proboscis 242 is disposed. Similarly, the proboscis 242 can have an inner diameter (a diameter of a surface at least partially defining the lumen 255) that is similar to or slightly larger than an outer diameter of a portion of the catheter 260, as described in further detail herein.

The first arm 243 and the second arm 250 of the lock 240 can be any suitable shape, size, and/or configuration. As shown in FIGS. 13 and 14, the first arm 243 has a first end portion 244, a second end portion 245 including a tab 246, and a pivot portion 247 disposed between the first end portion 244 and the second end portion 245. The tab 246 disposed at and/or formed by the second end portion 245 extends from the second end portion 245 toward, for example, the proboscis 242. In this manner, the tab 246 can selectively engage a portion of the PIV and/or a portion of an adapter coupled to the PIV to couple the lock 240 thereto, as described in further detail herein.

The pivot portion 247 of the first arm 243 extends from the coupler 241, proboscis 242, and/or second arm 250 in a lateral direction. The first end portion 244 and the second end portion 245 of the first arm 243 are proximal to the pivot portion 247 and distal to the pivot portion 247, respectively. As such, the first arm 243 can act as a lever or the like configured to pivot about an axis defined by the pivot portion 247 in response to an applied force. For example, in some instances, a user can exert a force on the first end portion 244 (e.g., toward the coupler 241) that is sufficient to pivot the first end portion 244 of the first arm 243 toward the coupler 241 (as indicated by the arrow AA in FIG. 14) and the second end portion 245 of the first arm 243 away from the proboscis 242 (as indicated by the arrow BB in FIG. 14), as described in further detail herein.

As described above with reference to the first arm 243, the second arm 250 of the lock 240 has a first end portion 251, a second end portion 252 including a tab 253, and a pivot portion 254 disposed between the first end portion 251 and the second end portion 252. In this embodiment, the first arm 243 and the second arm 250 are substantially similar in form and function and are arranged in opposite positions and orientations relative to the coupler 241 and proboscis 242 (e.g., the lock 240 is substantially symmetrical about its longitudinal axis). As such, the discussion of the first arm 243 similarly applies to the second arm 250 and thus, the second arm 250 is not described in further detail herein.

As described above, the lock 240 is configured to be coupled to the PIV and/or an adapter coupled to the PIV. For example, a user can exert a lateral force on the first end portion 244 of the first arm 243 and the first end portion 251 of the second arm 250 to pivot the first arm 243 and the second arm 250, respectively, from a first position toward a second position. The pivoting of the first arm 243, therefore, increases a space defined between the proboscis 242 and the second end portion 245 (and the tab 246) of the first arm 243. Similarly, the pivoting of the second arm 250 increases a space defined between the proboscis 242 and the second end portion 252 (and the tab 253) of the second arm 250. In this manner, the increased space between the proboscis 242 and the arms 243 and 250 is sufficient to allow a portion of the PIV and/or an adapter coupled to the PIV to be inserted within the space. Once the portion of the PIV and/or the adapter is in a desired position relative to the lock 240, the user can remove the force and in turn, the arms 243 and 250 pivot toward their respective first positions. As a result, the second end portions 245 and 252 are moved toward the proboscis 242 until the tabs 246 and 253, respectively, are placed in contact with a portion of the PIV and/or the adapter. The tabs 246 and 253 are configured to engage the portion of the PIV and/or adapter to temporarily couple the lock 240 to the PIV and/or adapter. In some embodiments, the lock 240 can be configured to establish three points of contact with the PIV and/or the adapter, namely, the tabs 246 and 253, and an outer surface of the proboscis 242 (as described above). In some embodiments, the tabs 246 and 253 can be configured to produce an audible output such as a click, a vibratory output such as a haptic bump, and/or the like when placed in contact with the portion of the PIV and/or adapter, which can indicate to a user that the lock 240 is properly coupled to the PIV and/or adapter.

As shown in FIG. 15, the proboscis 242 and the coupler 241 collectively define the lumen 255. The lumen 255 of the lock 240 defines an axis (not shown) that is aligned with and/or substantially co-axial with the axis defined by the second portion 215 of the inner volume 213. Thus, the lumen 255 of the lock 240 receives a portion of the catheter 260 when the transfer device 200 is transitioned between the first configuration and the second configuration. In some embodiments, the lumen 255 can have a size and/or shape that is based at least in part on a size and/or shape of the catheter 260. For example, the lumen 255 can have an inner diameter that is slightly larger than an outer diameter of at least a portion of the catheter 260. In such embodiments, the lock 240 can be and external guide or the like that can support and/or guide the catheter 260 as the catheter 260 is moved within the lumen 255, which in turn, can reduce and/or substantially prevent undesirable bending, kinking, flexing, and/or deforming of the catheter 260.

Although the lock 240 is shown and described above as including the proboscis 242, in other embodiments, a lock need not form a proboscis. For example, in some such embodiments, a lock can include a relatively short hub or the like configured to engage a portion of the PIV and/or an adapter coupled to the PIV. In some embodiments, a fluid transfer device can include and/or can be used with a proboscis or guide member (not formed with or by the lock) configured to be disposed, for example, between a PIV and an adapter such as an IV extension set. For example, such a proboscis or guide member can have an inner surface that is funnel shaped and/or is shaped similar to the inner surface of the proboscis 242. In this manner, the inner surface of such a proboscis and/or guide member can guide a portion of the catheter 260 as the catheter 260 is moved between the first position and the second position. In some embodiments, the lock 240 (including the proboscis 242) can be used in conjunction with such an external or separate proboscis and/or guide member. In some such embodiments, a portion of the proboscis 242 of the lock 240 can be inserted into the proboscis and/or guide member when the lock 240 is coupled to the adapter (e.g., IV extension set).

Figure 16:
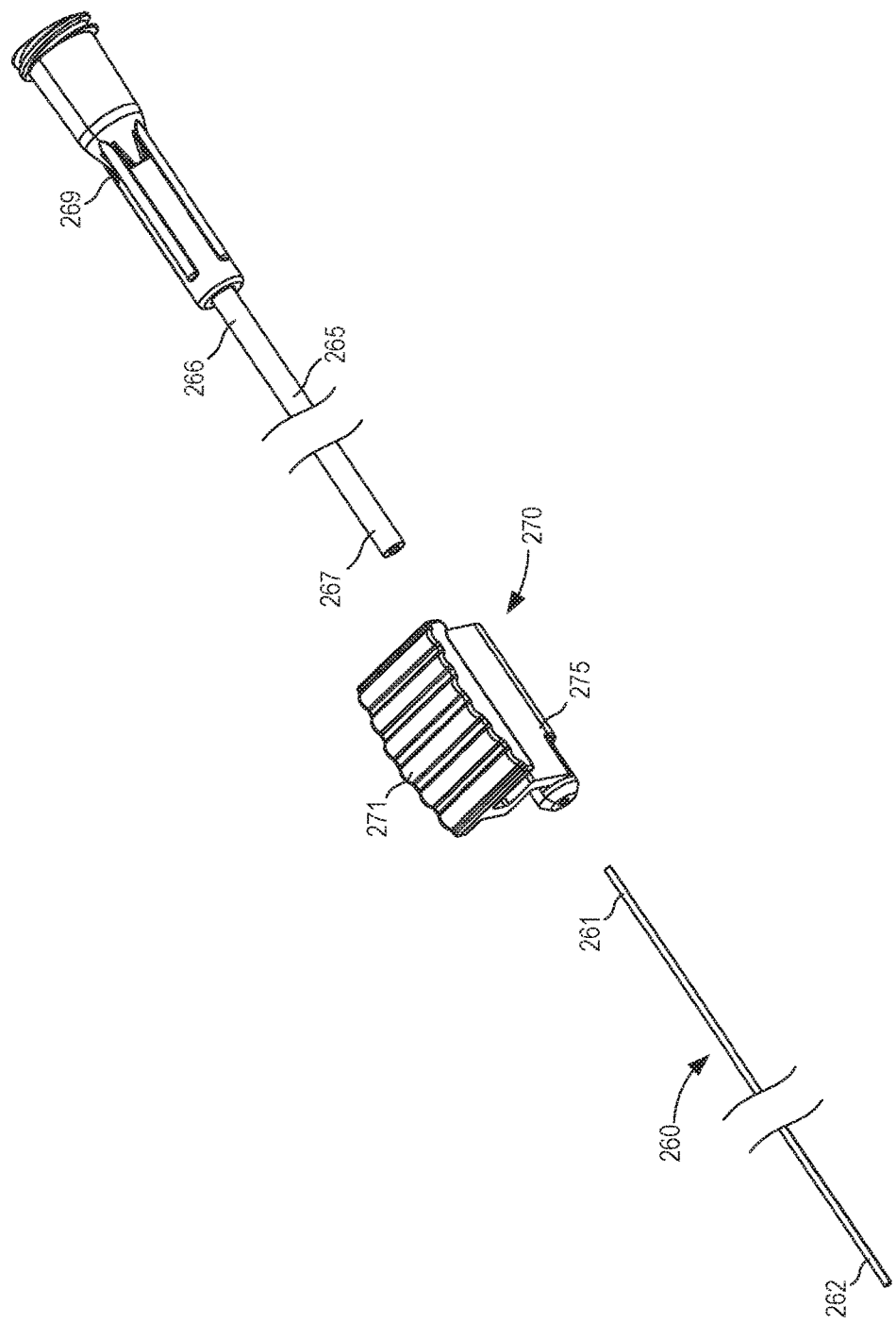
FIG. 16 is an exploded perspective view a catheter, a secondary catheter, and an actuator included in the fluid transfer device of FIG. 3.
Figure 17:
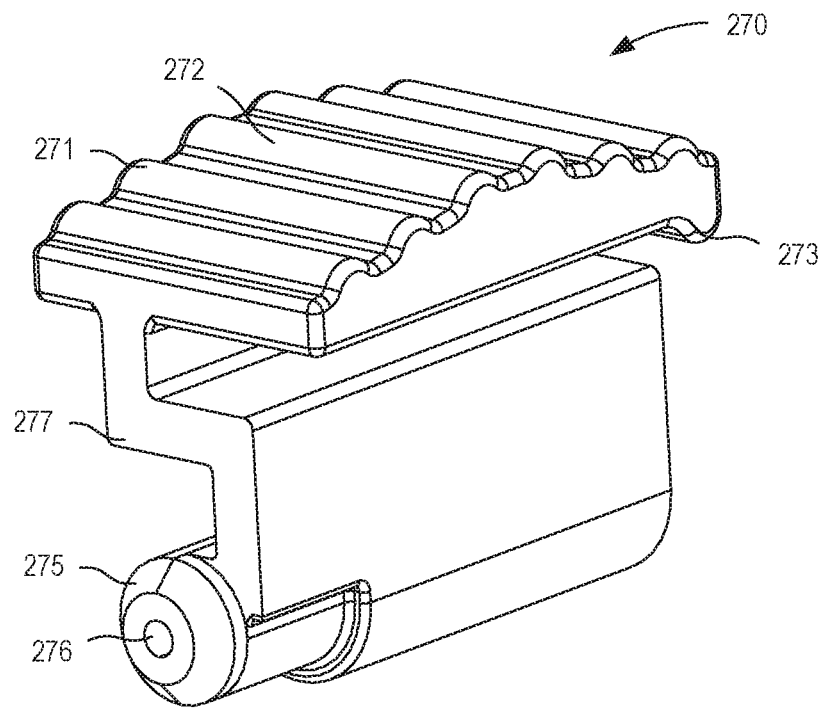
FIGS. 17-19 are a perspective view, a side view, and a front view, respectively, of the actuator illustrated in FIG. 16.

As described above, at least a portion of the catheter 260 and at least a portion of the secondary catheter 265 is movably disposed within the second portion 215 of the inner volume 213 defined by the introducer 210. As shown in FIG. 16, the catheter 260 has a proximal end portion 261 and a distal end portion 262 and defines a lumen 263 (see e.g., FIG. 24). The proximal end portion 261 of the catheter 260 is coupled to a second portion 275 of the actuator 270. In this manner, the actuator 270 can be moved relative to the introducer 210 to move the catheter 260 between a first position, in which the catheter 260 is disposed within the introducer 210 (e.g., the entire catheter 260 is disposed within the introducer 210 or within the introducer 210 and the lock 240) and a second position, in which the distal end portion of the catheter 260 is at least partially disposed in a position distal to the lock 240 and/or the PIV (not shown) when the lock 240 is coupled to the PIV, as described in further detail herein. The distal end portion 262 can be any suitable shape, size, and/or configuration and can define at least one opening in fluid communication the lumen 263. For example, in some embodiments, the distal end portion 262 of the catheter can be substantially similar to any of those described in U.S. Pat. No. 8,366,685 (referred to herein as the "'685 patent") entitled, "Systems and Methods for Phlebotomy Through a Peripheral IV Catheter," filed on Apr. 26, 2012, the disclosure of which is incorporated herein by reference in its entirety.

The catheter 260 can be any suitable shape, size, and/or configuration. For example, in some embodiments, at least a portion of the catheter 260 can have an outer diameter that is substantially similar to or slightly smaller than an inner diameter defined by the lumen 255 of the lock 240, as described above. In some embodiments, an outer surface of the catheter 260 can be configured to contact an inner surface of the lock 240 that defines at least a portion of the lumen 255. In this manner, an inner surface of the portion of the lock 240 defining the lumen 255 can guide the catheter 260 as the catheter 260 is moved between the first position and the second position. In some embodiments, such an arrangement can limit and/or can substantially prevent bending, deforming, and/or kinking of the catheter 260 as the catheter 260 is moved between the first position and the second position. Moreover, in some embodiments, the catheter 260 can have a length that is sufficient to place a distal surface of the catheter 260 in a desired position relative to a distal surface of the PIV when the catheter 260 is in the second position. In other words, the length of the catheter 260 can be sufficient to define a predetermined and/or desired distance between the distal surface of the catheter 260 and the distal surface of the PIV when the catheter 260 is in the second position, as described in further detail herein.

The catheter 260 can be formed from any suitable material or combination of materials, which in turn, can result in the catheter 260 having any suitable stiffness or durometer. For example, in some embodiments, the catheter 260 can be formed of a relatively flexible biocompatible material with a Shore durometer of approximately 20 Shore A to 50 Shore D; approximately 20 Shore A to 95 Shore D; approximately 70 Shore D to 85 Shore D, and/or any other suitable range of Shore durometer. In some embodiments, at least a portion of the catheter 260 can be formed of a braided material or the like, which can modify, change, and/or alter a flexibility of the catheter 260 in response to a bending force or the like. In other words, forming at least a portion of the catheter 260 from the braided material can increase an amount of deformation (in response to a bending force) of the catheter 260 prior buckling, kinking, and/or otherwise obstructing the lumen 263 of the catheter 260. Similarly, forming at least a portion of the catheter 260 of a braided material can result in a compression and/or deformation in response to a compression force exerted in a direction of a longitudinal centerline defined by the catheter 260 (e.g., an axial force or the like). In this manner, the catheter 260 can absorb a portion of force associated with, for example, impacting an obstruction or the like. In some instances, such an arrangement can reduce buckling and/or kinking of the catheter 260 as well as reduce and/or substantially prevent damage to vascular structures that may otherwise result from an impact of the catheter 260. Moreover, in some embodiments, forming at least a portion of the catheter 260 from the braided material, for example, can increase an amount of vibration transmitted through the catheter 260 in response to the portion of the actuator 270 advancing along the set of ribs 236 of the introducer 210 (as described above). While the catheter 260 is described above as including at least a portion formed of a braided material, in other embodiments, at least a portion of the catheter 260 can be formed of and/or can include a support wire, a stent, a fenestrated catheter, and/or the like such as those described in the '685 patent incorporated by reference above.

Figure 24:
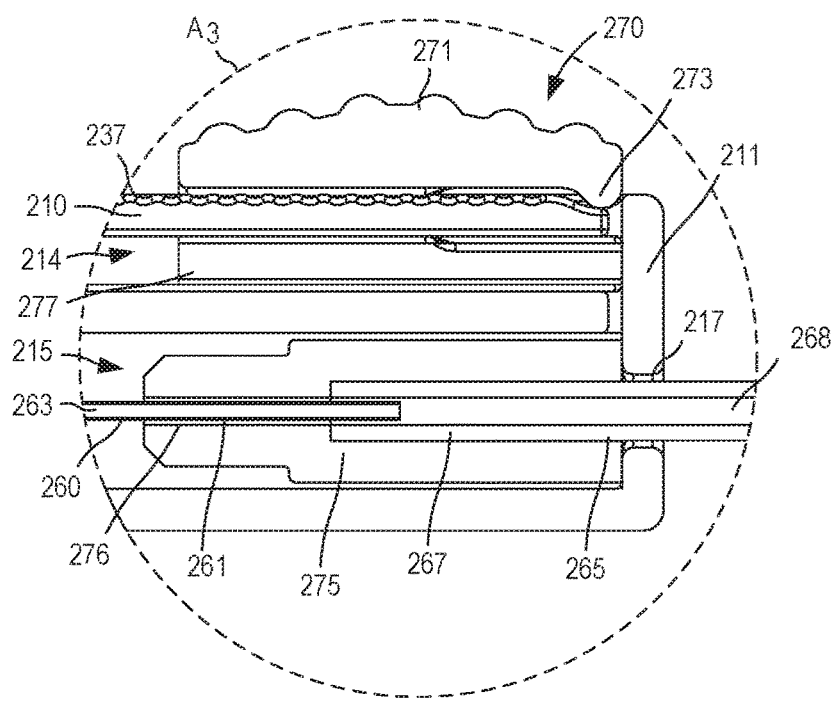
FIG. 24 is an enlarged cross-sectional view of a portion of the fluid transfer device identified by the region A3 in FIG. 22.

The secondary catheter 265 has a proximal end portion 266 and a distal end portion 267 and defines a lumen 268 (see e.g., FIG. 24). A portion of the secondary catheter 265 is disposed within and extends through the opening 217 of the introducer 210 (e.g., collectively defined by the notches 223 and 233 of the first member 220 and second member 230, respectively). As such, the proximal end portion 266 is at least partially disposed outside of the introducer 210 and the distal end portion 267 is at least partially disposed within the second portion 215 of the inner volume 213 defined by the introducer 210. As described above, the secondary catheter 265 can be moved within the opening 217 between a first position and a second position to selectively clamp, pinch, kink, bend, and/or otherwise deform a portion of the secondary catheter 265, which in turn, obstructs, pinches, kinks, closes, seals, etc. the lumen 268 of the secondary catheter 265. For example, the first position can be associated and/or aligned with a first portion of the opening 217 having a larger perimeter and/or diameter than a perimeter and/or diameter of a second portion of the opening 217 associated and/or aligned with the second position. Thus, a user can manipulate the secondary catheter 265 to occlude the lumen 268 of the secondary catheter 265, thereby limiting, restricting, and/or substantially preventing a flow of a fluid therethrough.

As shown in FIG. 16, the proximal end portion 266 of the secondary catheter 265 is coupled to and/or otherwise includes a coupler 269. The coupler 269 is configured to physically and fluidically couple the secondary catheter 265 to any suitable device such as, for example, a fluid reservoir, fluid source, syringe, evacuated container holder (e.g., having a sheathed needle or configured to be coupled to a sheathed needle), pump, and/or the like. The distal end portion 267 of the secondary catheter 265 is at least partially disposed within the second portion 215 of the inner volume 213 defined by the introducer 210 and is coupled to the second portion 275 of the actuator 270. In some embodiments, the secondary catheter 265 can have a larger diameter than the catheter 260 such that the proximal end portion 261 of the catheter 260 is at least partially disposed within the lumen 268 defined by the secondary catheter 265 when the catheter 260 and the secondary catheter 265 are coupled to the second portion 275 of the actuator 270. In some embodiments, such an arrangement can, for example, reduce and/or substantially prevent leaks associated with fluid flowing between the catheter 260 and the secondary catheter 265. In some embodiments, such an arrangement can also limit, reduce, and/or substantially prevent hemolysis of a volume of blood as the volume of blood flows through the catheter 260 and the secondary catheter 265. In this manner, when the coupler 269 is coupled to a fluid reservoir, fluid source, syringe, evacuated container, pump, etc., the secondary catheter 265 establishes fluid communication between the reservoir, source, pump, etc. and the catheter 260.

The actuator 270 of the transfer device 200 is coupled to the catheter 260 can be moved along a length of the introducer 210 to transition the transfer device 200 between its first configuration, in which the catheter 260 is in the first position, and its second configuration, in which the catheter 260 is in the second position. The actuator 270 can be any suitable shape, size, and/or configuration. For example, in some embodiments, the actuator 270 can have a size and shape that is associated with and/or based at least in part on a size and/or shape of the introducer 210.

As shown in FIGS. 17-20, the actuator 270 includes a first portion 271, the second portion 275, and a wall 277 extending therebetween. The first portion 271 of the actuator 270 is at least partially disposed within the first portion 214 of the inner volume 213 defined by the introducer 210 and the second portion 275 of the actuator 270 is disposed within the second portion 215 of the inner volume 213, as described above. The first portion 271 of the actuator 270 includes an engagement member 272. The arrangement of the actuator 270 is such that the engagement member 272 is disposed outside of the introducer 210 while the rest of the first portion 271 is within the first portion 214 of the inner volume 213 defined by the introducer 210. As such, the engagement member 272 can be engaged and/or manipulated by a user (e.g., by a finger or thumb of the user) to move the actuator 270 relative to the introducer 210. In some embodiments, the engagement member 272 can include a set of ridges and/or any suitable surface finish that can, for example, increase the ergonomics of the actuator 270 and/or transfer device 200.

The engagement member 272 includes a tab 273 disposed at or near a proximal end portion of the engagement member 272. The tab 273 can be any suitable tab, rail, ridge, bump, protrusion, knob, roller, slider, etc. that extends from a surface of the engagement member 272. The tab 273 is configured to selectively engage the outer surface 235 of the second member 230 of the introducer 210. More specifically, the tab 273 is in contact with the ribs 236 formed by the second member 230 and moves along each successive rib as the actuator 270 is moved along a length of the introducer 210.

Figure 18:
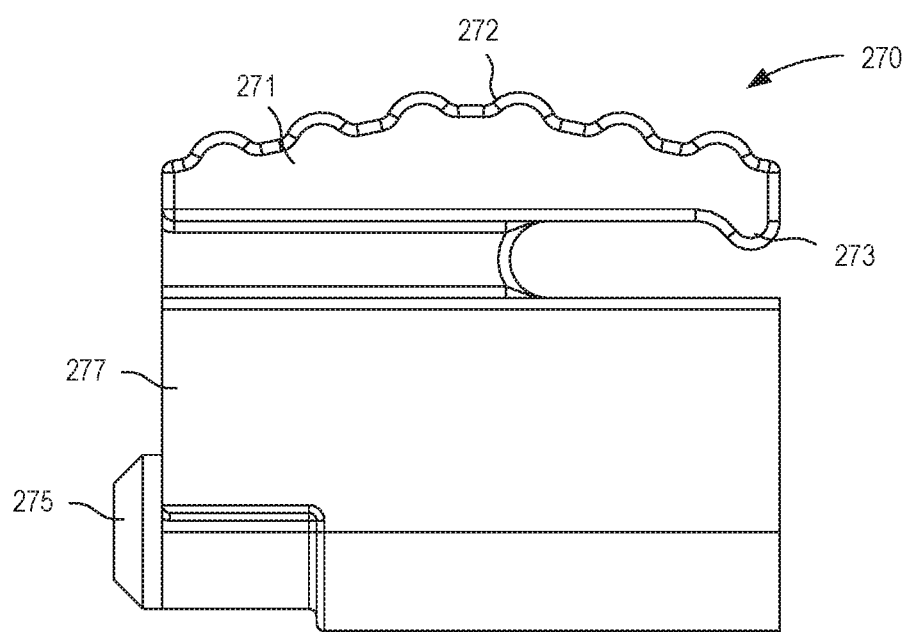

As described above with reference to the set of ribs 236 of the second member 230, the tab 273 can have any suitable shape, size, and/or configuration. For example, as shown in FIG. 18, the tab 273 can include a substantially rounded surface that can be moved along the set of ribs 236. In some embodiments, the size and/or shape of the tab 273 is based at least in part on a size and/or shape of the ribs 236 such that a desired surface area of the tab 273 is in contact with the ribs 236 as the actuator 270 is moved relative to the introducer 210. In some embodiments, an amount of friction defined between the set of ribs 236 and the tab 273 can be based at least in part on a surface area of the tab 273 that is in contact with the set of ribs 236. Moreover, an amount of friction defined between the set of ribs 236 and the tab 273 can be based at least in part on a position of the tab 273 relative to each rib. For example, in some embodiments, an amount of friction defined between the tab 273 and a rib can increase at the tab 273 moves closer to, for example, a local maxima and can decrease as the tab 273 moves away from the local maxima. In some embodiments, the tab 273 can have a size and/or shape that allows the tab 273 to move with substantially less friction between each adjacent rib (e.g., between adjacent local maximums). In other words, the arrangement of the tab 273 and the set of ribs 236 can allow for a desired amount of "play" between adjacent ribs.

With the first portion 237 of the set of ribs 236 having a smaller size than the second portion 238 of the set of ribs 236, a first portion or first surface area of the tab 273 can be in contact with the first portion 237 of the set of ribs 236 and a second portion or second surface area of the tab 273 can be in contact with the second portion 238 of the set of ribs 236. In this manner, the tab 273 can move along the first portion 237 with a first set of characteristics and can move along the second portion 238 with a second set of characteristics different from the first set of characteristics. In some embodiments, for example, a force sufficient to move the tab 273 along the second portion 238 of the set of rib 236 can be greater than a force otherwise sufficient to move the tab 273 along the first portion 237 of the set of ribs 236. In some embodiments, the movement of the tab 273 along the second portion 238 of the set of ribs 236 can result in, for example, a larger amount of vibration of the actuator 270 than an amount of vibration otherwise resulting from the movement of the tab 273 along the first portion 237 of the set of ribs 236. Similarly, the shape of the tab 273 can be such that the tab 273 moves along the set of ribs 236 in the distal direction in response to an applied force that is insufficient to move the tab 273 along the set of ribs 236 in the proximal direction. For example, as shown in FIG. 18, the tab 273 has an asymmetric shape, wherein a proximal surface of the tab 273 has a greater pitch than a pitch of its distal surface.

While the engagement member 272 and tab 273 are particularly shown and described above, in other embodiments, an actuator can include an engagement member and/or tab having any suitable configuration. For example, while the tab 273 is shown as being disposed at or near a proximal end portion of the engagement member 272, in other embodiments, an engagement member can include a first tab disposed at or near a proximal end portion and a second tab disposed at or near a distal end portion, each of which can be selectively in contact with a set of ribs disposed on an outer surface of an introducer. In some embodiments, a space defined between a surface of the wall 277 and a surface of the engagement member 272 can be increased or decreased, which can result in an increase or decrease in an amount of travel of the actuator 270 relative to the introducer 210 in a direction other than an axial direction. That is to say, the increase or decrease in space between the surface of the wall 277 and a surface of the engagement member 272 can result in, for example, an increase or decrease of an amount the actuator 270 can "tilt" relative to the introducer 210. In other embodiments, the arrangement of the engagement member 272, the tab 273, and/or the set of ribs 236 of the introducer 210 can be modified, altered, tuned, adjusted, and/or otherwise changed such that the actuator 270 moves relative to the introducer 210 with a desired set of characteristics. For example, in some embodiments, the arrangement of the actuator 270 and/or introducer 210 can increase or decrease an amount the actuator 270 vibrates as it is moved relative to the introducer 210, increase or decrease an amount of force sufficient to move the actuator 270 relative to the introducer 210, increase or decrease an amount of movement of the actuator 270 relative to the introducer 210 in any suitable direction other than the axial direction (e.g., proximal direction or distal direction), and/or the like.

Figure 19:
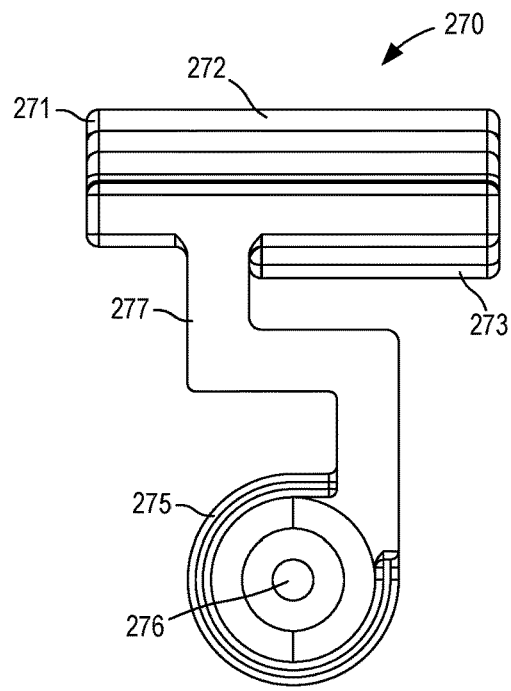
Figure 20:
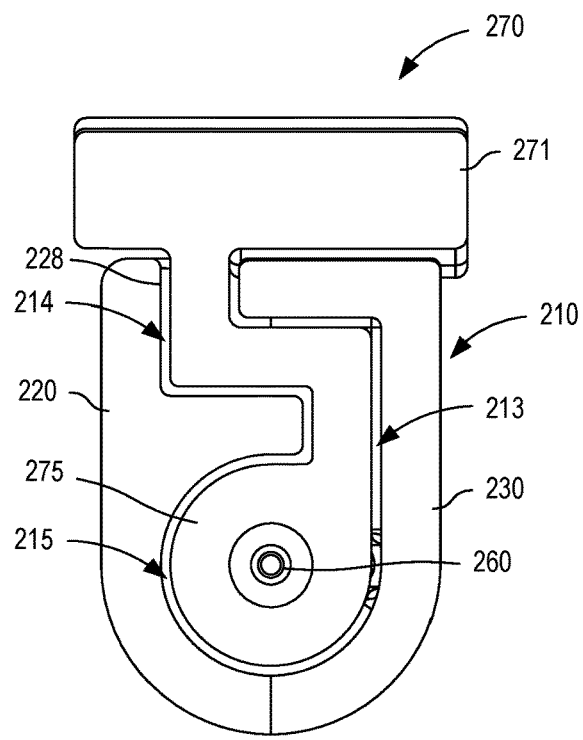
FIG. 20 is a cross-sectional view of the fluid transfer device taken along the line 20-20 in FIG. 4.
Figure 21:
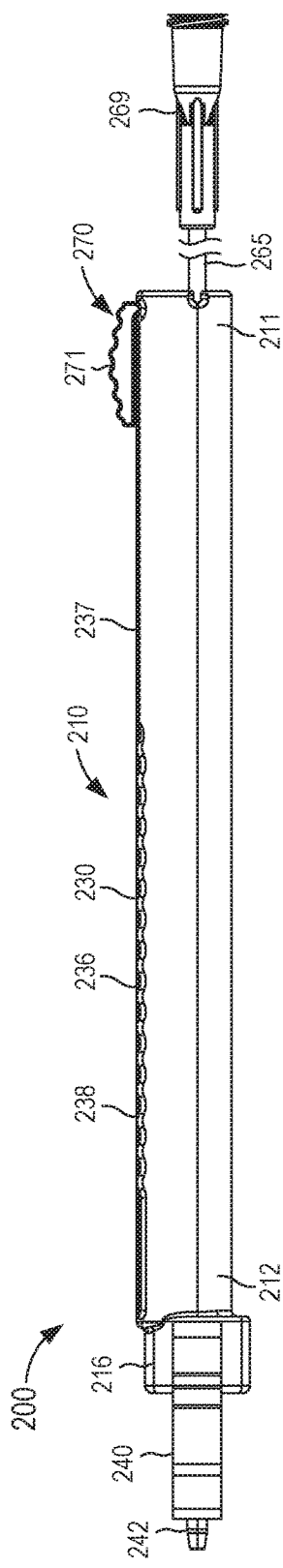
FIG. 21 is a side view of the fluid transfer device of FIG. 3 in the first configuration.
Figure 22:
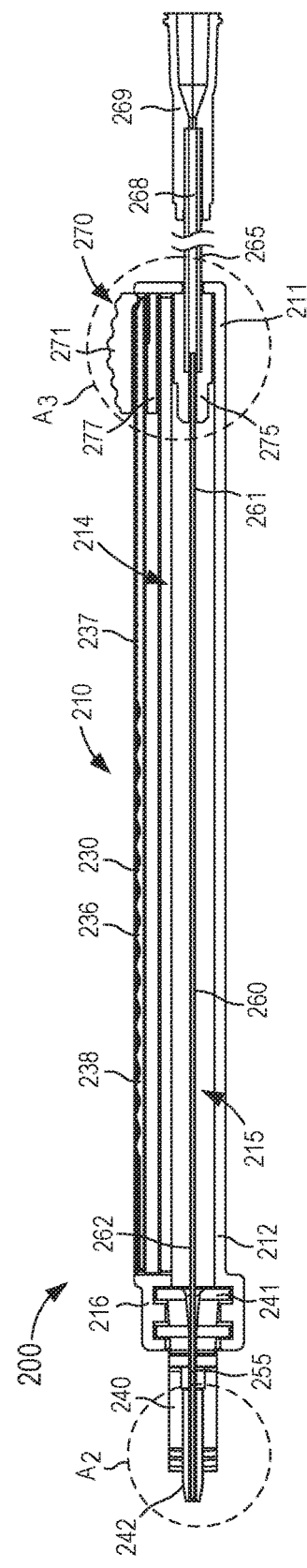
FIG. 22 is a cross-sectional view of the fluid transfer device in the first configuration taken along the line 22-22 in FIG. 3.
Figure 23:
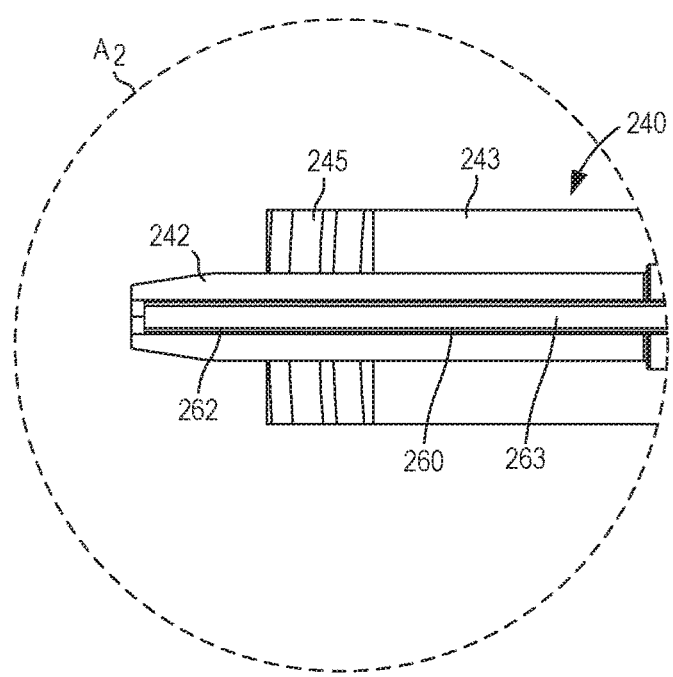
FIG. 23 is an enlarged cross-sectional view of a portion of the fluid transfer device identified by the region A2 in FIG. 22.

As shown, for example, in FIGS. 19 and 20, the second portion 275 has a cross-sectional shape that is based at least in part on a cross-sectional shape of the second portion 215 of the inner volume 213 defined by the introducer 210 (e.g., at least a partially circular cross-sectional shape). In this manner, the inner surface 223 of the first member 220 and the inner surface 233 of the second member 230 can support and/or guide the second portion 275 of the actuator 270 as the actuator 270 moves relative to the introducer 210. As shown, the second portion 275 defines an opening 276 configured to receive a proximal end portion 261 of the catheter 260 and a distal end portion 267 of the secondary catheter 265. In some embodiments, the proximal end portion 261 of the catheter 260 can form a friction fit with an inner surface of the second portion 275 of the actuator 270 when the proximal end portion 261 is disposed in the opening 276. Similarly, the distal end portion 267 of the secondary catheter 265 can form a friction fit with an inner surface of the second portion 275 of the actuator 270 when the distal end portion 267 is disposed in the opening 276. As such, the catheter 260 and the secondary catheter 265 can be maintained in a fixed position relative to the actuator 270 and thus, move concurrently with the actuator 270 as the actuator 270 is moved relative to the introducer 210.

The wall 277 of the actuator 270 couples the first portion 271 of the actuator 270 to the second portion 275 of the actuator 270. As shown in FIGS. 19 and 20, the wall 277 has a tortuous cross-sectional shape that is based at least in part on the tortuous cross-sectional shape of the inner volume 213 defined by the introducer 210. In this manner, the first portion 271 of the actuator 270 can define an axis that is parallel to but offset from an axis defined by the second portion 275 of the actuator 270. In some embodiments, for example, the wall 277 can have a substantially S-shaped or an at least partially S-shaped cross-sectional shape. In some embodiments, the wall 277 can form, for example, a dogleg or the like. The tortuous cross-sectional shape of the wall 277 (and thus, the actuator 270) is such that the second portion 275 of the actuator 270 cannot be viewed (e.g., is out of the line of sight) via the first portion 214 of the inner volume 213 defined by the introducer 210. Similarly, the catheter 260 cannot be viewed via the first portion 214 of the inner volume 213 defined by the introducer 210 when the catheter 260 is in the first position. That is to say, the geometry of the actuator 270 and/or the introducer 210 (e.g., the tortuous cross-sectional shape of the inner volume 213, the height and/or width of the introducer 210, etc.) is configured such that the catheter 260 is at least partially isolated within the second portion 215 of the inner volume 213 when the catheter 260 is in the first position. In this manner, the structure of the introducer 210 and/or the actuator 260 can protect and/or isolate the catheter 260 from a volume outside of the introducer 210, which in turn, can limit and/or substantially prevent contamination of the catheter 260. For example, in some embodiments, the introducer 210 and/or the actuator 270 can act as a "sneeze guard" or the like configured to at least partially isolate the catheter 260 at least when the catheter 260 is in the first position.

Referring now to FIGS. 21-29, the transfer device 200 can be in the first configuration prior to use and can be transitioned by a user (e.g., a doctor, physician, nurse, technician, phlebotomist, and/or the like) from the first configuration (FIGS. 21-24) to the second configuration (FIGS. 27-29) to dispose at least the distal end portion 262 of the catheter 260 in a distal position relative to the introducer 210 (e.g., within an indwelling PIV (not shown) or distal to the indwelling PIV). The transfer device 200 is in the first configuration when the catheter 260 is disposed in the first position 260 within the introducer 210. In some embodiments, substantially the entire catheter 260 is disposed within the introducer 210 when the catheter 260 is in the first position. In such embodiments, the introducer 210 can include the seal or the like (as described above) that can substantially seal the distal end portion 212 of the introducer 210 to isolate the catheter 260 within the second portion 215 of the inner volume 213. In the embodiment shown in FIGS. 22 and 23, however, the catheter 260 is disposed within the introducer 210 and the lock 240 when catheter 260 is in the first position. While the seal is described above as being included in the distal end portion 212 of the introducer 210, in other embodiments, the lock 240 can include a seal or the like that can form a substantially fluid tight seal with an inner surface of the lock 240 that defines the lumen 243. Thus, the seal disposed within the lock 240 can isolate the catheter 260 within the second portion 215 of the inner volume 213. In still other embodiments, the introducer 210 and/or the lock 240 need not include a seal. For example, in some embodiments, a PIV and/or an adapter (e.g., extension set) coupled to the PIV can include a seal that is transitioned from a closed configuration to an open configuration when the lock 240 is coupled thereto. Although not shown, in some embodiments, the catheter 260 can be disposed within a flexible sheath or the like that can maintain the catheter 260 in a substantially sterile environment while the catheter 260 is in the first position (e.g., such as those embodiments in which the introducer 210 and/or lock 240 do not include a seal).

The actuator 270 is disposed in a proximal position when the transfer device 200 is in the first configuration, as shown in FIG. 24. In some embodiments, the tab 273 of the first portion 271 of the actuator 270 can be disposed within a recess or detent or otherwise in contact with a proximal most rib configured to temporarily maintain the actuator 270 in the proximal position until a force is exerted (e.g., by the user) to move the actuator 270 in the distal direction. Moreover, as described above, a portion of the secondary catheter 265 is disposed in the opening 217 defined by the introducer such that the distal end portion 267 is at least partially disposed in the second portion 215 of the inner volume 213 and coupled to the second portion 275 of the actuator 270 while the proximal end portion 266 of the secondary catheter 265 is disposed outside of the introducer 210 (see e.g., FIGS. 21 and 22).

With the transfer device 200 in the first configuration, the user can manipulate the transfer device 200 to couple the lock 240 to an indwelling PIV and/or to an adapter coupled to the PIV (e.g., an extension set or the like). For example, in some embodiments, the user can exert a force sufficient to pivot the first arm 243 and the second arm 250 of the lock 240 such that a portion of the PIV and/or the adapter can be inserted into the space defined between the arms 243 and 250 and, for example, the proboscis 242. In some embodiments, the proboscis 242 can be inserted into the PIV and/or the adapter when the lock 240 is coupled thereto. For example, in some embodiments, a portion of the proboscis 242 can be inserted into a hub or basket of the PIV and/or adapter. As described above, in some embodiments, the proboscis 242 that is sufficiently long to dispose at least a portion of the proboscis 242 within the PIV, which in turn, supports and/or provides structural rigidity to the PIV. Once the PIV and/or adapter is disposed in the desired position relative to the lock 240, the user can remove the force on the arms 243 and 250 of the lock 240, which in turn, move toward proboscis 242 until the tab 246 of the first arm 243 and the tab 253 of the second arm 250 are placed in contact with a surface of the PIV and/or adapter. In some embodiments, the arrangement of the lock 240 is such that the tabs 246 and 253 and the proboscis 242 form three points of contact with the PIV and/or adapter that collectively coupled the lock 240 thereto.

With the transfer device 200 coupled to the PIV and/or adapter, the user can engage the engagement member 272 of the first portion 271 of the actuator 270 to move the actuator 270 relative to the introducer 210, which in turn, moves the catheter 260 from the first position (e.g., disposed within the introducer 210) toward the second position. In this manner, the catheter 260 is moved through the second portion 215 of the inner volume 213 and the lumen 255 of the lock 240 and as such, at least the distal end portion 262 of the catheter 260 is disposed outside of and distal to the lock 240, as indicated by the arrow CC in FIG. 25. In some embodiments, the arrangement of the lumen 255 of the lock 240 and the catheter 260 can be such that an inner surface of the lock 240 defining the lumen 255 contacts, supports, and/or otherwise guides the catheter 260 as the catheter 260 is moved in the distal direction toward the second position. Moreover, in some embodiments, moving the catheter 260 from the first position toward the second position can be operable to transition the seal (e.g., disposed in the lock 240) from a closed or sealed configuration to an open configuration. In other embodiments, the user can manipulate the transfer device 200 (e.g., prior to moving the catheter 260 from the first position) to transition the seal from the sealed configuration to the open configuration. For example, in some embodiments, the user can increase a pressure within at least a portion of the transfer device 200 (e.g., the catheter 260 and/or the lock 240) beyond a predetermined threshold to transition the seal to the open configuration. In some embodiments, the seal can be a one way valve (e.g., a positive pressure valve or seal) that can be transitioned from the sealed configuration to the open configuration, for example, when a pressure exerted on a proximal portion of the seal exceeds a pressure exerted on a distal portion of the seal (e.g., venous pressure exerted on the seal).

As described above, the arrangement of the actuator 270 and the introducer 210 is such that advancing the actuator 270 relative to the introducer 210 advances the tab 273 along the outer surface 235 and more specifically, the set of ribs 236 of the second member 230 of the introducer 210. As shown, for example, in FIG. 26, the tab 273 is in contact with the set of ribs 236, which can produce a vibration of the actuator 270 as the actuator 270 is moved relative to the introducer 210. In some instances, the vibration of the actuator 270 can produce, for example, a haptic, tactile, and/or audible output that can provide an indication associated with a position of the distal end portion 262 of the catheter 260 relative to the introducer 210, lock 240, and/or PIV. For example, in some embodiments, the tab 273 of the actuator 270 and the set of ribs 236 can collectively produce a "click" sound as the tab 273 moves past each rib. In some embodiments, the introducer 210 can include indicia or the like that can indicate to the user the relative position of the distal end portion 262 of the catheter 260. In other embodiments, the amount of times the actuator 270 has vibrated due to being moved relative to that number of ribs can be associated with and/or otherwise provide an indication of the relative position of the distal end portion 262 of the catheter 260.

In some instances, the user can stop moving the actuator 270 relative to the introducer 210 based on the haptic, tactile, and/or audible output indicating a desired placement of the distal end portion 262 of the catheter 260 relative to the PIV (e.g., the second position). In other words, the catheter 260 can be placed in the second position prior to the actuator 270 being advanced, for example, to a distal most position. As described in further detail herein, the catheter 260 is disposed in the second position when the distal end portion 262 of the catheter 260 is placed in a desired position relative to a distal end portion of the PIV. In some instances, for example, a distal end of the catheter 260 can be substantially flush with a distal end of the PIV when the catheter 260 is in the second position. In other instances, the distal end of the catheter 260 can extend a predetermined distance beyond the distal end of the PIV (e.g., distal to the distal end of the PIV). In still other instances, the distal end of the catheter 260 can be disposed within the PIV (e.g., proximal to the distal end of the PIV) when the catheter 260 is in the second position.

Figure 27:
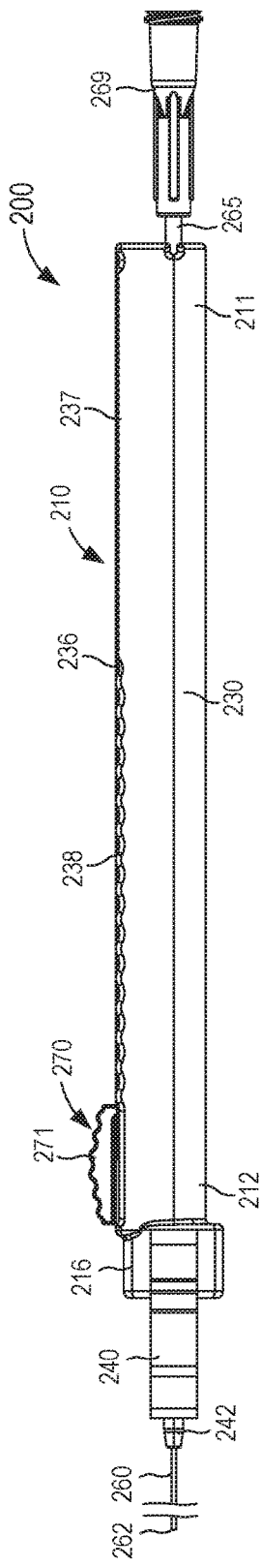
FIG. 27 is a side view of the fluid transfer device of FIG. 3 in the second configuration.
Figure 28:
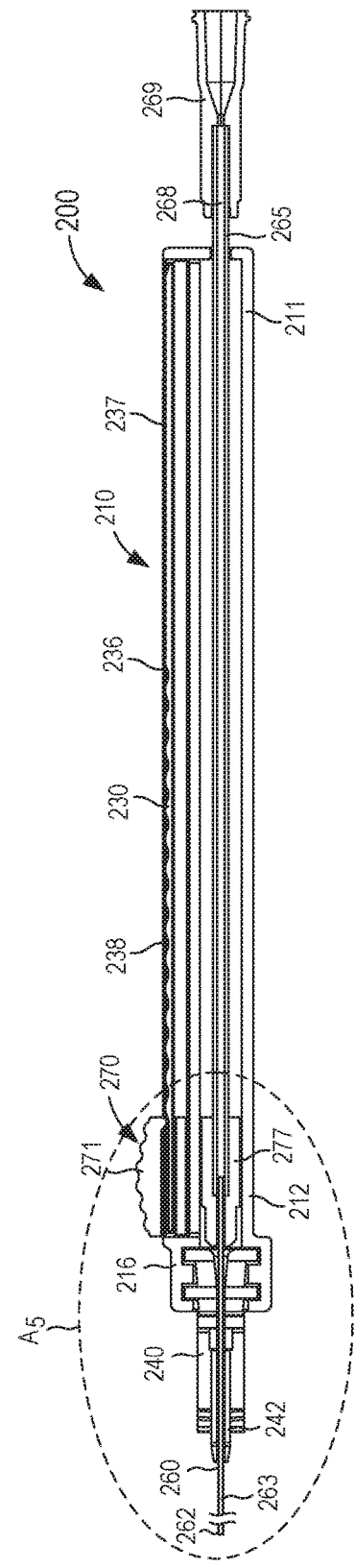
FIG. 28 is a cross-sectional view of the fluid transfer device in the second configuration taken along the line 22-22 in FIG. 3.
Figure 29:
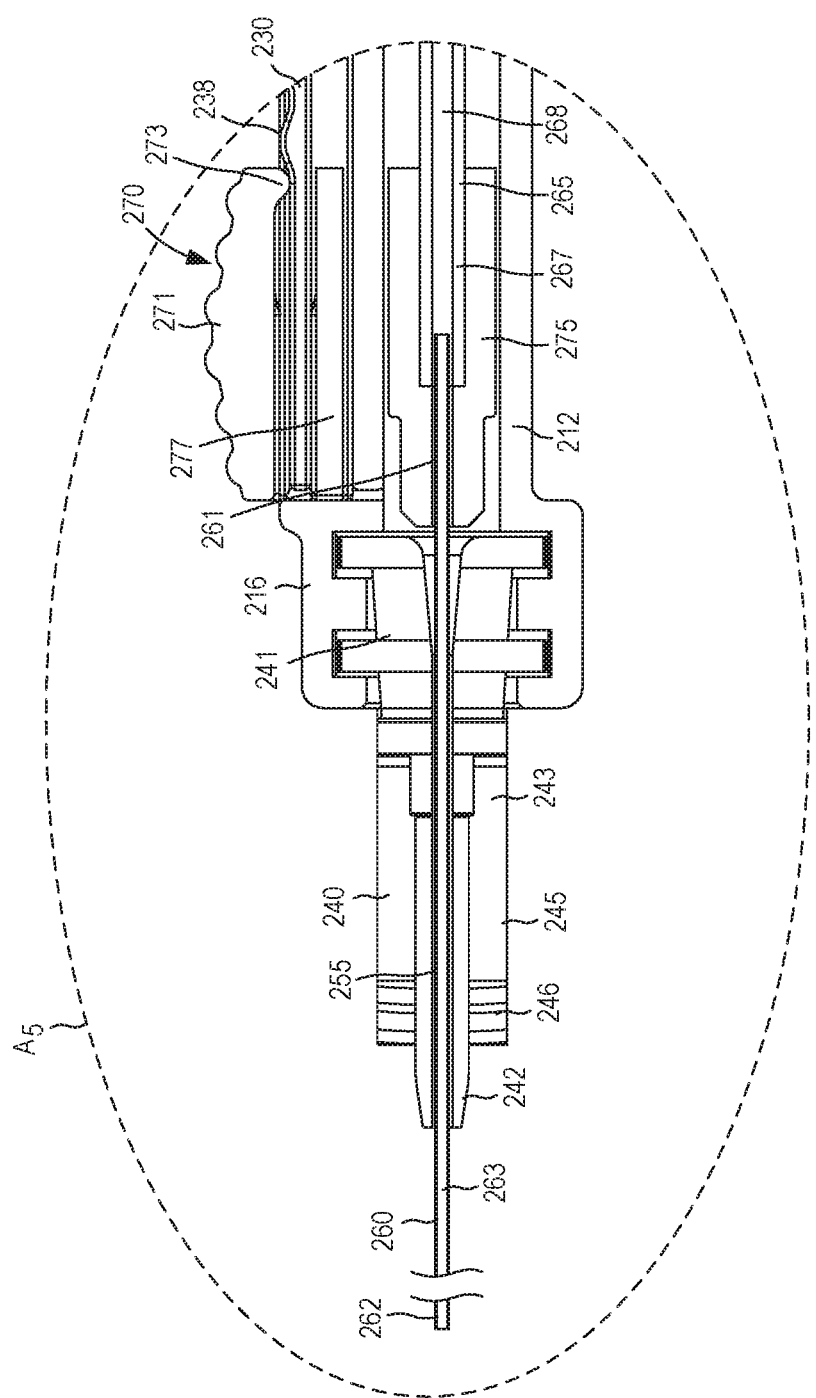
FIG. 29 is an enlarged cross-sectional view of a portion of the fluid transfer device identified by the region A5 in FIG. 28.

As shown in FIGS. 27-29, in some instances, the catheter 260 can be in the second position when the actuator 270 is in a distal most position. In this manner, the distal surface of the catheter 260 is positioned within the vein at a predetermined distance beyond the distal surface of the catheter 260. In some instances, placing the distal surface of the catheter 260 the predetermined and/or desired distance from the distal surface of the PIV can, for example, place the distal surface of the catheter 260 in a position within a vein that is substantially free from debris (e.g., fibrin/blood clots) otherwise surrounding the distal end portion of the PIV.

In some instances, the indwelling PIV can substantially occlude at least a portion of the vein within which the PIV is disposed. As such, PIVs are often suited for delivering a fluid rather than aspirating blood. The venous system, however, is a capacitance system and thus, reroutes blood flow through a different vein (e.g., forms a bypass around the occlusion or substantial occlusion). Moreover, the alternate venous structure typically rejoins the vein in which the PIV is disposed at a given distance downstream of the PIV and thus, delivers at least portion of the flow of blood that would otherwise be flowing through the vein in which the PIV is disposed. Similarly, veins typically have many branch vessels coupled to thereto that similarly deliver a flow of blood to the vein within which the PIV is disposed.

As such, in some instances, the predetermined and/or desired distance between the distal surface of the catheter 260 and the distal surface of the PIV can be sufficient to place the distal surface of the catheter 260 downstream of one or more branch vessels in fluid communication with the vein within which the PIV is disposed. In other words, the distal surface of the catheter 260 can extend beyond the distal surface of the catheter 260 such that at least one branch vessel is disposed between the distal surface of the catheter 260 and the distal surface of the PIV when the catheter 260 is in the second position. Therefore, with the lumen 263 of the catheter 260 extending through the proximal end portion 261 and the distal end portion 262 of the catheter 260, placing the distal surface of the catheter 260 the predetermined and/or desired distance from the distal surface of the PIV places the lumen 263 of the catheter 260 in fluid communication with a portion of the vein receiving a substantially unobstructed or unrestricted flow of blood (e.g., unobstructed by the PIV and/or debris associated with the indwelling of the PIV).

In some instances, for example, the predetermined and/or desired distance can be between about 0.0 millimeters (e.g., the distal surfaces are flush) and about 100 millimeters (mm). In other embodiments, the predetermined and/or desired distance can be between about 10 mm and about 90 mm, between about 20 mm and about 80 mm, between about 30 mm and about 70 mm, between about 30 mm and about 60 mm, between about 40 mm and about 50 mm, or between any other suitable range or subranges therebetween. In some embodiments, for example, the transfer device 200 can be configured such that the actuator 270 can move about 95 mm along the introducer 210 (e.g., the transfer device 200 has a 95 mm stroke) to position the distal surface of the catheter 260 at about 40 mm beyond the distal surface of the PIV to which the transfer device 200 is coupled. In other embodiments, for example, the transfer device 200 can have a 47 mm stroke that positions the distal surface of the catheter 260 at about 20 mm beyond the distal surface of the PIV to which the transfer device 200 is coupled. In still other embodiments, the transfer device 200 can have any suitable stroke length to position the distal surface of the catheter 260 at the predetermined and/or desired distance from the distal surface of the PIV.

Although the predetermined and/or desired distance is described above as being a positive distance, that is, the distal surface of the catheter 260 is distal to the distal surface of the PIV, in other embodiments, the predetermined and/or desired distance can be associated with the distal surface of the catheter 260 being in a proximal position relative to the distal surface of the PIV (e.g., a negative distance). For example, in some instances, the predetermined and/or desired distance can be between about 0.0 mm (e.g., the distal surfaces are flush) to about −50 mm, between about −10 mm and about −40 mm, between about −20 mm and about −30 mm, or between any other suitable range or subranges therebetween. In some instances, the predetermined and/or desired distance can be less than −50 mm (e.g., the distal surface of the catheter 260 is more than 50 mm proximal to the distal surface of the PIV). In some instances, the catheter 260 can be placed in the second position such that the distal end portion 262 of the catheter 260 remains within the PIV in a position distal to, for example, a kink or the like. For example, in some instances, indwelling PIVs can have one or more portions that are kinked such as a portion of the PIV where the peripheral intravenous catheter couples to a hub. In such instances, the predetermined and/or desired distance can be such that the distal surface of the catheter 260 is distal to the portion of the PIV that forms the kink (e.g., where the peripheral intravenous catheter couples to the hub). In some such instances, placing the distal surface of the catheter 260 distal to the kinked portion of the PIV but remaining within the PIV can result in a fluid flow path being sufficiently unrestricted to allow blood to be aspirated through the catheter 260.

With the catheter 260 in the second position (e.g., with the transfer device 200 in the second configuration shown, for example, in FIGS. 25 and 26 or FIGS. 27-29), the user can establish fluid communication between a fluid reservoir, fluid source, syringe, and/or the like and the catheter 260. For example, as described above, in some embodiments, the user can physically and fluidically couple the coupler 269 of the secondary catheter 265 to a fluid reservoir, fluid source, syringe, and/or the like. Although described as establishing fluid communication between the catheter 260 and the fluid reservoir or fluid source after placing the catheter 260 in the second position, in other embodiments, the user can establish fluid communication between the catheter 260 and the fluid reservoir or fluid source prior to moving the actuator 270 relative to the introducer 210. With the catheter 260 in fluid communication with the fluid reservoir and/or fluid source, the transfer device 200 can then transfer a fluid from the patient or transfer a fluid to the patient via the catheter 260 extending through and beyond the PIV. For example, in some instances, the user can physically and fluidically couple the transfer device 200 to a fluid reservoir, evacuated container, syringe, and/or the like and then can aspirate a volume of blood from the vein based at least in part on disposing the distal surface of the catheter 260 at the predetermined and/or desired distance beyond the distal surface of the PIV.

In other instances, the user can physically and fluidically coupled the transfer device 200 to a fluid source or the like and then can deliver a volume of fluid from the fluid source to a portion of the vein at a position downstream of the PIV that receives a substantially uninhibited and/or unrestricted flow of blood. In some instances, disposing the distal surface of the catheter 260 at the predetermined and/or desired distance beyond the distal surface of the PIV, for example, can reduce potential harm associated with infusion of caustic drugs. For example, by positioning the distal surface of the catheter 260 within a portion of the vein receiving a flow of blood that would otherwise be inhibited and/or restricted by the indwelling PIV, the caustic drug can be entrained in the flow of blood and delivered to the target location. As such, a volume of the caustic drug is not retained within the debris or otherwise disposed in a position within the vein receiving little blood flow.

In some instances, once a desired amount of blood has been collected and/or once a desired volume of a drug has been delivered to the patient, the user can move the actuator 270 in the proximal direction, thereby placing the transfer device 200 in a third (used) configuration. In the third configuration, the catheter 260 can be disposed within the introducer 210 (e.g., distal to the seal or the like) and isolated therein. For example, in some embodiments, the actuator 270 can be placed in it proximal most position, in which the catheter 260 is in the first position. Moreover, once the actuator 270 and catheter 260 are in the desired position, the user can, for example, manipulate the secondary catheter 265 within the opening 217 such that a surface of the introducer 210 that defines the smaller portion of the opening 217 contacts and clamps the secondary catheter 265. As such, the lumen 268 of the secondary catheter 265 can be substantially obstructed, occluded, blocked, pinched, etc. to limit and/or substantially prevent a flow of fluid therethrough. In some instances, clamping the secondary catheter 265 as described, for example, can reduce and/or substantially prevent fluid from leaking through the secondary catheter 265. In some instances, the transfer device 200 can then be decoupled from the fluid reservoir, fluid source, syringe, etc. and safely discarded.

FIG. 30 is a flowchart illustrating a method 10 of using a fluid transfer device to transfer a fluid through a peripheral intravenous line, according to an embodiment. The method includes coupling a lock of the fluid transfer device to an indwelling peripheral intravenous line (PIV), at 11. The fluid transfer device can be any suitable device configured for fluid transfer through a PIV. For example, in this embodiment, the fluid transfer device can be substantially similar to the fluid transfer device 200 described above with reference to FIGS. 3-29. As such, the fluid transfer device includes an introducer coupled to the lock, a catheter movably disposed in the introducer, and an actuator coupled to the catheter and in contact with an outer surface of the introducer. In some embodiments, the introducer includes a first member and a second member that collectively form the introducer. In such embodiments, the second member can have an outer surface that defines a set of ribs or the like, as described above with reference to the second member 230 in FIGS. 7-12. In this manner, the actuator can be in contact with the ribs formed by the second member of the introducer. Moreover, as described above with reference to the transfer device 200, the introducer can define an inner volume having a tortuous cross-sectional shape configured to at least partially isolate the catheter disposed in the inner volume from a volume outside of the introducer.

With the lock coupled to the PIV (and/or an adapter coupled to the PIV), the actuator is moved relative to the introducer to advance the catheter from a first position, in which the catheter is disposed within at least one of an inner volume defined by the introducer or the lock, toward a second position, in which at least a portion of the catheter is disposed beyond at least a portion of the PIV, at 12. In this manner, the catheter can be advanced, for example, in the distal direction. In some embodiments, the lock can include an inner surface that defines a lumen configured to receive the catheter as the catheter is moved toward the second position. In some embodiments, the inner surface of the lock can contact, support, and/or otherwise guide the catheter as the catheter is moved in the distal direction toward the second position.

As described above with reference to the transfer device 200 in some embodiments, the arrangement of the actuator and the introducer is such that advancing the actuator relative to the introducer advances a portion of the actuator along the ribs formed by the outer surface of the introducer. In some embodiments, moving the actuator along the ribs can produce a vibration of the actuator, which in turn, can produce, for example, a haptic, tactile, and/or audible output. Thus, an indication associated with a position of a distal end portion of the catheter as the actuator moves the catheter from the first position toward the second position is provided to the user, at 13. For example, in some embodiments, the actuator and the set of ribs can collectively produce a "click" sound, a haptic vibration, and/or the like. In some embodiments, the introducer can include indicia or the like that can indicate to the user the relative position of the distal end portion of the catheter. In other embodiments, the amount of times the actuator has vibrated due to being moved along the ribs can be associated with and/or otherwise provide an indication of the relative position of the distal end portion of the catheter.

Based at least in part on the indication, the catheter is placed in the second position such that the distal end portion of the catheter is disposed at a predetermined and/or desired distance beyond at least a portion of the PIV (e.g., beyond a distal surface of the PIV), at 14. For example, the catheter can be placed in the second position after moving the actuator at least a portion of the length of the introducer. In some embodiments, the catheter can be disposed in the second position when the actuator is placed in a distal most position. As described above with reference to the transfer device 200, in some instances, the predetermined and/or desired distance beyond the portion of the PIV can position a distal surface of the catheter within a portion of the vein that is substantially free from debris (e.g., fibrin/blood clots) otherwise surrounding a distal end portion of the PIV. Similarly, in some instances, disposing the distal end portion of the catheter at the predetermined and/or desired distance from, for example, the distal end portion of the PIV can place the lumen of the catheter in fluid communication with a portion of the vein receiving a substantially unobstructed or unrestricted flow of blood (e.g., unobstructed by the PIV and/or debris associated with the indwelling of the PIV), as described in detail above. In this manner, a user can couple the transfer device to a fluid reservoir and/or fluid source to transfer fluid from and/or to, respectively, the patient.

Although not shown in FIGS. 1 and 2 with reference to the transfer device 100 or FIGS. 3-29 with reference to the transfer device 200, the transfer devices 100 and 200 can be coupled to any suitable peripheral intravenous line (PIV). In some instances, use of a PIV can include coupling the PIV to an IV extension set and/or an adapter (e.g., a single port adapter, a Y-adapter, a T-adapter, or the like). Thus, while the transfer devices 100 and 200 are described herein as being coupled to a PIV, it should be understood that the transfer devices 100 and 200 can be coupled to either a PIV or an adapter coupled thereto based on the situation and/or configuration. The transfer devices 100 and 200 can be configured to couple to any suitable commercially available PIV, adapter, and/or extension set. For example, while the first arm 243 and the second arm 250 of the lock 240 are shown (e.g., in FIGS. 13 and 14) and described above as having a given shape and/or configuration, in other embodiments, a lock can include a first arm and a second arm that have a size, shape, and/or configuration that can allow the lock to be coupled to various PIVs, adapters, and/or extension sets. By way of example, in some embodiments, the arms of a lock can be rounded, bent, bowed, widened, and/or the like to allow the lock to receive a portion of any suitable PIV, adapter, and/or extension set. In some embodiments, the arrangement of the arms 243 and 250 of the lock 240 can allow the lock 240 to be rotated substantially 360° about any suitable PIV, adapter, and/or extension set when coupled thereto. Moreover, while the proboscis 242 is shown and described above as having a particular size and/or shape, in other embodiments, a lock can include a proboscis that has any suitable length (e.g., longer or shorter than the proboscis 242), width (e.g., wider or narrower than the proboscis 242), and/or shape (e.g., curved, tapered, flared, etc.). In some embodiments, a proboscis can have a surface finish or feature such as one or more threads, flighting (e.g., an auger flighting), ribs, grooves, and/or the like.

The embodiments described herein can be used to transfer fluid from a patient or to the patient by accessing a vein via an indwelling PIV. As described above, the transfer devices 100 and/or 200, for example, can be manipulated to place a distal surface of a catheter at a predetermined and/or desired distance from a distal surface of the PIV. In some instances, the embodiments described herein allow for efficient blood draw while maintaining the integrity of the sample. While extracting blood, the transfer devices 100 and/or 200 can be configured to receive and/or produce a substantially laminar (e.g., non-turbulent or low turbulent) flow of blood through the transfer device 100 and/or 200, respectively, to reduce and/or substantially prevent hemolysis of the blood as the blood flows through the transfer devices 100 and/or 200, respectively.

While the embodiments described herein can be used in a variety of settings (ER, in-patient, etc.), the following scenario of withdrawing a sample volume of blood from a patient is provided by way of example. In some instances, for example, a peripheral intravenous line and/or catheter (PIV) is inserted into a vein of a patient following standard guidelines and an extension set and/or adapter is attached. The PIV can remain within the vein for an extended period and can provide access to the vein for the transfer of fluids (e.g., saline, blood, drug compounds, etc.) to the patient. When it is time to draw blood, a user (e.g., nurse, physician, phlebotomist, and/or the like) can stop the transfer of fluid to the patient, if it is transferring fluid, for approximately 1-5 minutes to allow the fluid to disperse from the blood-drawing site. To draw the blood sample, the user attaches a transfer device (e.g., the transfer devices 100 and/or 200) to a port and/or suitable portion of the extension set and/or adapter and transitions the transfer device to from a first configuration (e.g., a storage configuration) to a second configuration, in which a portion of a catheter included in the transfer device extends through the peripheral IV and into the vein.

As described in detail above with reference to the transfer device 200, an end of the catheter can be disposed at a predetermined and/or desired distance from an end of the PIV when the transfer device is in the second configuration to place the catheter in fluid communication with a portion of the vein that receives an unobstructed and/or uninhibited flow of blood. For example, the end of the catheter can be in a distal position relative to the end portion of the PIV and at least one branch vessel, valve, and/or the like in fluid communication with the vein. Once the catheter is in the desired position, the user can attach one or more negative pressure collection containers, tubes, and/or syringes to the transfer device to extract a volume of blood. In some instances, the volume of blood can be a first volume of blood that can be discarded and/or at least temporarily stored apart from a subsequent sample volume of blood (e.g., typically a volume of about 1-3 milliliters (mL) but up to 8-10 mL of blood can be a "waste" or "pre-sample" volume). In some instance, the waste volume can include contaminants, non-dispersed residual fluids, and/or the like. After the collective of the waste volume, the user can couple one or more negative pressure containers (e.g., sample containers) to the transfer device to collect a desired blood sample volume. Once the sample volume is collected, the transfer device can be transitioned from the second configuration toward the first configuration and/or a third configuration (e.g., a "used" configuration). The transfer device can then be decoupled from the extension set and/or adapter and safely discarded. In some instances, after collecting the sample volume but prior to transitioning the transfer device from the second configuration, the waste or pre-sample volume, for example, can be reinfused into the vein.

In some instances, the transfer devices described herein can be assembled during one or more manufacturing processes and packaged in a pre-assembled configuration. For example, in some instances, the transfer device 200 can be assembled by coupling the catheter 260 and the secondary catheter 265 to the actuator 270; positioning the catheter 260, secondary catheter 265, and actuator 270 relative to the first member 220 or second member 230 of the introducer 210; coupling the first member 220 and the second member 230 to form the introducer 210 with the actuator 270 and at least a portion of the catheter 260 and secondary catheter 265 disposed in the inner volume 213 of the introducer 210; and coupling the lock 240 to the introducer 210. In some instances, the assembly of the transfer device 200 can be performed in a substantially sterile environment such as, for example, an ethylene oxide environment, or the like. In other embodiments, the transfer devices described herein can be packaged in a non-assembled configuration (e.g., a user can open the package and assemble the components to form the transfer device). The components of the transfer devices can be packaged together or separately. In some embodiments, the transfer devices can be packaged with, for example, a PIV, an extension set, a Y-adapter or T-adapter, and/or any other suitable component.

While various embodiments have been described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above.

While the embodiments have been particularly shown and described, it will be understood that various changes in form and details may be made. For example, while the transfer device 200 is shown and described above as including the catheter 260 and the secondary catheter 265, each of which being coupled to the actuator 270, in other embodiments, the transfer device 200 can include a single catheter (e.g., the catheter 260). For example, in some embodiments, at least the second portion 275 of the actuator 270 can be configured to transition between an open configuration and a closed configuration. In such embodiments, the catheter 260 can be placed in a desired position relative to the second portion 275 when the second portion 275 is in the open configuration. The second portion 275 can then be transitioned from the open configuration to the closed configuration to retain at least a portion of the catheter 260 within the opening 276 defined by the second portion 275. In such embodiments, the second portion 275 and the portion of the catheter 260 disposed in the opening 276 can form a friction fit operable to retain the catheter 260 in a fixed position relative to the actuator 270. Moreover, the friction fit defined between the second portion 275 of the actuator 270 and the catheter 260 can isolate a portion of the catheter 260 that is distal to the actuator 270 from a portion of the catheter 260 that is proximal to the actuator 270. Thus, the portion of the catheter 260 that is proximal to the actuator 270 can extend through the opening 217 and at least partially outside of the introducer 210 without contaminating the portion of the catheter 260 distal to the actuator 270.

Any of the aspects and/or features of the embodiments shown and described herein can be modified to affect the performance of the transfer device. For example, the ribs in the set of ribs 236 of the introducer 210 and the tab 273 of the actuator 270 can have any suitable shape, size, configuration, and/or arrangement to produce a desired set of characteristics associated with the movement of the actuator 270 relative to the introducer 210, as described above. By way of another example, any of the components of the transfer devices 100 and/or 200 can be formed from any suitable material that can result in a desired hardness, durometer, and/or stiffness of that component. For example, in some embodiments, at least the proboscis 242 of the lock 240 can be formed from a substantially rigid material such as a metal or hard plastic. In such embodiments, forming at least the proboscis 242 from the substantially rigid material can increase the structure support provided by the proboscis 242 to a PIV when the proboscis 242 is at least partially disposed therein. Similarly, the proboscis 242 can provide support to and/or otherwise can guide the catheter 260 when the catheter 260 is moved therethrough.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed is:

1. An apparatus, comprising:
   a catheter having a proximal end portion and a distal end portion and defining a lumen extending through the proximal end portion and the distal end portion;
   an introducer having a proximal end portion and a distal end portion, the introducer defining an inner volume having a first portion and a second portion, the inner volume having a tortuous cross-sectional shape relative to a plane perpendicular to a longitudinal axis of the introducer such that an axis defined by the first portion of the inner volume is parallel to and offset from an axis defined by the second portion of the inner volume, the first portion being adjacent to a slot defined by the introducer, the second portion being offset from the first portion in a transverse direction along the plane, the second portion configured to movably receive the catheter, the distal end portion of the introducer configured to be coupled to an indwelling peripheral intravenous line; and
   an actuator having a first portion extending through the slot to be movably disposed in the first portion of the inner volume and a second portion movably disposed in the second portion of the inner volume, the second portion of the actuator being coupled to the catheter, the actuator configured to move relative to the introducer to move the catheter between a first position and a second position, the catheter disposed within the introducer when in the first position, the distal end portion of the catheter disposed beyond the distal end portion of the introducer such that at least a portion of the catheter is disposed within the indwelling peripheral intravenous line when the catheter is in the second position and the introducer is coupled to the indwelling peripheral intravenous line.

2. The apparatus of claim 1, wherein the introducer includes a first member and a second member, the first member configured to couple to the second member to collectively form the introducer, an inner surface of the first member and an inner surface of the second member collectively defining the inner volume of the introducer when the first member is coupled to the second member.

3. The apparatus of claim 1, wherein the first portion of the actuator and the second portion of the actuator collectively have the tortuous cross-sectional shape.

4. The apparatus of claim 1, wherein the catheter is configured to reduce fluid flow restrictions present within the peripheral intravenous line as the catheter is moved from the first position to the second position, the distal end portion of the catheter being disposed within the peripheral intravenous line when the catheter is in the second position such that the distal end portion of the catheter is distal to a portion of the peripheral intravenous line otherwise restricted by the fluid flow restrictions.

5. The apparatus of claim 1, further comprising:
   a lock coupled to the distal end portion of the introducer, the lock configured to contact a portion of the peripheral intravenous line to couple the distal end portion of the introducer to the peripheral intravenous line, the lock defines a lumen, an axis defined by the lumen of the lock is substantially coaxial with the axis of the second portion of the inner volume, the lumen is configured to receive a portion of the catheter as the catheter is moved between the first position and the second position.

6. The apparatus of claim 1, further comprising:
   an adapter disposed between the distal end portion of the introducer and the peripheral intravenous line, the adapter having an outer surface configured to be placed in contact with an inner surface of the peripheral intravenous line, the adapter having an inner surface defining a lumen, the lumen is configured to receive a portion of the catheter as the catheter is moved between the first position and the second position, the inner surface of the adapter is configured to guide the catheter as the catheter is moved between the first position and the second position.

7. The apparatus of claim 1, wherein the proximal end portion of the catheter is coupled to the actuator such that the distal end portion of the catheter is distal to actuator, the actuator is configured to couple to a distal end portion of a secondary catheter such that a proximal end portion of the secondary catheter is proximal to the actuator,
   the secondary catheter defining a lumen in fluid communication with the lumen defined by the catheter, the proximal end portion of the secondary catheter is configured to fluidically couple to at least one of a fluid reservoir, a fluid source, or a syringe to place the lumen of the catheter in fluid communication with at least one of the fluid reservoir, the fluid source, or the syringe.

8. The apparatus of claim 7, wherein the proximal end portion of the introducer defines an opening, the opening including a first portion having a first size and a second portion having a second size smaller than the first size,
   a portion of the secondary catheter is movably disposed within the opening, the secondary catheter is configured to move between a first position, in which the secondary catheter is disposed in the first portion of the opening, and a second position, which the secondary catheter is disposed in the second portion of the opening, a surface of the introducer defining at least the second portion of the opening configured to contact the secondary catheter to substantially clamp the lumen of the secondary catheter when the secondary catheter is in the second position.

9. The apparatus of claim 1, wherein an inner surface of the introducer forming at least a portion of the tortuous cross-sectional shape of the inner volume is disposed in a line of sight defined between the slot and the second portion of the inner volume.

10. The apparatus of claim 1, wherein an inner surface of the introducer forming at least a portion of the tortuous cross-sectional shape of the inner volume is disposed in a line of sight defined between the slot and the catheter coupled to the second portion of the actuator.

11. The apparatus of claim 1, wherein the first portion of the actuator is configured to extend through the slot to be partially disposed outside of the inner volume.

12. The apparatus of claim 11, wherein an outer surface of the introducer forms a plurality of ribs, each rib from the plurality of ribs being distributed along a length of the introducer, the first portion of the actuator including a tab configured to move along the plurality of ribs when the actuator is moved relative to the introducer.

13. An apparatus, comprising:
a catheter having a proximal end portion and a distal end portion and defining a lumen extending through the proximal end portion and the distal end portion;
an introducer having a proximal end portion and a distal end portion, the introducer defining an inner volume having a first portion and a second portion, the first portion being adjacent to a slot defined by the introducer, the second portion configured to movably receive the catheter, the inner volume having a tortuous cross-sectional shape relative to a plane perpendicular to a longitudinal axis of the introducer such that an axis defined by the first portion is parallel to and offset from an axis defined by the second portion, the second portion being offset from the first portion in a transverse direction along the plane such that an inner surface of the introducer defining at least a portion of the tortuous cross-sectional shape of the inner volume is disposed in a line of sight defined between the slot and the catheter disposed in the second portion of the inner volume;
an actuator having a first portion and a second portion, the first portion of the actuator disposed outside of the inner volume defined by the introducer and in contact with an outer surface of the introducer, the second portion of the actuator disposed within the inner volume defined by the introducer and coupled to the catheter, the actuator configured to move relative to the introducer to move the catheter between a first position and a second position; and
a lock coupled to the distal end portion of the introducer, the lock having a proboscis and defining a lumen extending through the proboscis, the lock configured to couple the introducer to an indwelling peripheral intravenous line, the proboscis configured to extend through a lumen defined by the indwelling peripheral intravenous line when the lock couples the introducer thereto, the lumen of the proboscis configured to receive a portion of the catheter as the catheter is moved from the first position, in which the catheter is disposed within the inner volume of the introducer, to the second position, in which the distal end portion of the catheter extends beyond the indwelling peripheral intravenous line when the lock couples the introducer thereto, an inner surface of the proboscis configured to guide the catheter as the catheter is moved from the first position to the second position.

14. The apparatus of claim 13, wherein the distal end portion of the introducer includes a seal configured to transition from a closed configuration to an open configuration in response to a change in pressure within the inner volume, the seal being in the closed configuration when the catheter is in the first position.

15. The apparatus of claim 13, wherein the lock includes a seal disposed in the lumen defined by the proboscis, the seal being in a closed configuration and the catheter being disposed in a proximal position relative to the seal when the catheter is in the first position.

16. The apparatus of claim 13, wherein a proximal end portion of the peripheral intravenous line is coupled to an adapter, the adapter defines a lumen and includes a seal disposed in the lumen,
the lock is configured to be coupled to the adapter to couple the introducer to the peripheral intravenous line, a portion of the proboscis is disposed in the lumen defined by the adapter and is configured to transition the seal from a closed configuration to an open configuration when the lock is coupled to the adapter.

17. The apparatus of claim 13, wherein the proboscis has an outer surface defining an outer diameter of the proboscis, the outer surface of the proboscis configured to selectively contact an inner surface defining at least a portion of the lumen of the peripheral intravenous line to support at least a portion the peripheral intravenous line.

18. The apparatus of claim 13, wherein the lock includes a first arm disposed on a first side of the proboscis and a second arm disposed on a second side of the proboscis opposite the first side of the proboscis, the first arm and the second arm are configured to pivot relative to the proboscis in response to a force exerted on the first arm and the second arm, respectively.

19. The apparatus of claim 13, wherein the lock includes a first arm disposed on a first side of the proboscis and a second arm disposed on a second side of the proboscis opposite the first side of the proboscis, a portion of the first arm and a portion of the second arm are each configured to deform when the lock is coupled to the peripheral intravenous line.

20. The apparatus of claim 13, wherein the lock includes a first arm disposed on a first side of the proboscis, the first arm includes a tab, the lock includes a second arm disposed on a second side of the proboscis opposite the first side of the proboscis, the second arm includes a tab, the tab of the first arm and the tab of the second arm are each configured to engage the peripheral intravenous line to couple the lock to the peripheral intravenous line.

21. The apparatus of claim 20, wherein the proboscis has an outer surface defining an outer diameter of the proboscis, the outer surface of the proboscis configured to selectively contact an inner surface defining at least a portion of the lumen of the peripheral intravenous line when the proboscis is disposed within the lumen defined by the peripheral intravenous line,
the tab of the first arm of the lock, the tab of the second arm of the lock, and the outer surface of the proboscis establishing at least three points of physical contact operable to couple the lock to the peripheral intravenous line.

22. The apparatus of claim 13, wherein the peripheral intravenous line is a first peripheral intravenous line having a first configuration, the lock is configured to couple to at least one of the first peripheral intravenous line or a second peripheral intravenous line disposed in a portion of a patient, the second peripheral intravenous line having a second configuration different from the first configuration, the lock configured to couple to at least one of the first peripheral intravenous line or the second peripheral intravenous line such that the lock can be rotated 360 degrees relative to the first peripheral intravenous line or the second peripheral intravenous line.

23. An apparatus, comprising:
a catheter having a proximal end portion and a distal end portion and defining a lumen extending through the proximal end portion and the distal end portion;
an introducer having a first member and a second member coupled to the first member, the second member having an outer surface forming a plurality of ribs, the first member and the second member collectively defining an inner volume and a slot in communication with the inner volume, the inner volume including a first portion adjacent to the slot and a second portion configured to receive the catheter, the inner volume having a tortuous cross-sectional shape relative to a plane perpendicular to a longitudinal axis of the introducer, the second portion being offset from the first portion in a transverse direction along the plane such that a surface of the first member is disposed in a line of sight defined between the slot and the catheter disposed in the second portion, a distal end portion of the introducer configured to be coupled to an indwelling peripheral intravenous line; and
an actuator having a first portion and a second portion, the actuator operatively coupled to the introducer, the first portion of the actuator disposed outside of the inner volume, the first portion including a surface in contact with the outer surface of the second member, the second portion of the actuator extending through the slot and disposed within the inner volume, the second portion of the actuator being coupled to the catheter, the actuator configured to move relative to the introducer to move the catheter between a first position, in which the catheter is disposed within the introducer, and a second position, in which the distal end portion of the catheter is disposed beyond at least a portion of the indwelling peripheral intravenous line when the introducer is coupled to the indwelling peripheral intravenous line, the surface of the first portion of the actuator configured to move along the plurality of ribs as the actuator moves the catheter between the first position and the second position, the surface of the actuator and the plurality of ribs providing a haptic output to a user associated with a position of the distal end portion of the catheter.

24. The apparatus of claim 23, wherein at least a portion of the catheter is formed of a flexible braided material.

25. The apparatus of claim 23, wherein the haptic output produced in response to the surface of the actuator being moved along the plurality of ribs is a vibration of at least in portion of the actuator.

26. The apparatus of claim 23, wherein an inner surface of the first member and an inner surface of the second member collectively define the inner volume of the introducer.

27. The apparatus of claim 26, wherein the inner surface of the first member obstructs the line of sight between the slot and the catheter disposed within the second portion of the inner volume.

28. The apparatus of claim 23, wherein the plurality of ribs formed by the second member includes a first plurality of ribs and a second plurality of ribs, each rib from the first plurality of ribs has a first size, each rib from the second plurality of ribs has a second size different from the first size.

29. The apparatus of claim 28, wherein the surface of the first portion of the actuator is configured to move along the first plurality of ribs with a first set of characteristics, the surface of the first portion of the actuator is configured to move along the second plurality of ribs with a second set of characteristics different from the first set of characteristics.

30. The apparatus of claim 28, wherein the surface of the actuator and each rib from the first plurality of ribs collectively produce a first haptic output as the surface of the actuator is moved relative to each rib from the first plurality of ribs, the surface of the actuator and each rib from the second plurality of ribs collectively produce a second haptic output as the surface of the actuator is moved relative to each rib from the second plurality of ribs, the second haptic output is different from the first haptic output.

31. The apparatus of claim 28, wherein the first plurality of ribs are uniformly distributed along a first length of the second member, the second plurality of ribs are uniformly distributed along a second length of the second member, the first length of the second member being proximal to the second length of the second member.

32. The apparatus of claim 31, wherein the first size is smaller than the second size.

33. The apparatus of claim 31, wherein the plurality of ribs includes the first plurality of ribs, the second plurality of ribs, and a third plurality of ribs, the third plurality of ribs are uniformly distributed along a third length of the second member, the third length of the second member being distal to the second length of the second member.

34. The apparatus of claim 23, wherein a size of each rib from the plurality of ribs can increase with each successive rib from the plurality of ribs from a first size of a proximal most rib from the plurality of ribs to a second size of a distal most rib from the plurality of ribs.

35. The apparatus of claim 23, wherein the plurality of ribs is a first plurality of ribs, the first member of the introducer has an outer surface forming a second plurality of ribs, a local maxima of each rib from the first plurality of ribs being offset from a local maxima of each rib from the second plurality of ribs, a local minima of each rib from the first plurality of ribs being offset from a local minima of each rib from the second plurality of ribs.

36. The apparatus of claim 23, wherein each rib from the plurality of ribs has an asymmetric shape, the surface of the first portion of the actuator is configured to move in the distal direction along the plurality of ribs with a first set of characteristics, the surface of the first portion of the actuator is configured to move in the proximal direction along the plurality of ribs with a second set of characteristics different from the first set of characteristics.

37. An apparatus, comprising:
a catheter having a proximal end portion and a distal end portion and defining a lumen extending through the proximal end portion and the distal end portion;

an introducer having a first member and a second member coupled to the first member, the first member having an outer surface forming a first plurality of ribs and the second member having an outer surface forming a second plurality of ribs, a local maxima of each rib from the first plurality of ribs being offset from a local maxima of each rib from the second plurality of ribs, a local minima of each rib from the first plurality of ribs being offset from a local minima of each rib from the second plurality of ribs, the first member and the second member collectively defining an inner volume and a slot in communication with the inner volume, the inner volume configured to receive the catheter, a distal end portion of the introducer configured to be coupled to an indwelling peripheral intravenous line; and an actuator having a first portion and a second portion, the actuator operatively coupled to the introducer, the first portion of the actuator disposed outside of the inner volume, the first portion including a surface in contact with the outer surface of the second member, the second portion of the actuator extending through the slot and disposed within the inner volume, the second portion of the actuator being coupled to the catheter, the actuator configured to move relative to the introducer to move the catheter between a first position, in which the catheter is disposed within the introducer, and a second position, in which the distal end portion of the catheter is disposed beyond at least a portion of the peripheral intravenous line when the introducer is coupled to the peripheral intravenous line, the surface of the first portion of the actuator configured to move along the plurality of ribs as the actuator moves the catheter between the first position and the second position, the surface of the actuator and the plurality of ribs providing a haptic output to a user associated with a position of the distal end portion of the catheter.

* * * * *